US008828993B2

(12) United States Patent
Portnoy et al.

(10) Patent No.: US 8,828,993 B2
(45) Date of Patent: Sep. 9, 2014

(54) PSYCHOTROPIC AGENTS HAVING GLUTAMATE NMDA ACTIVITY

(71) Applicant: Ramot At Tel-Aviv University Ltd., Tel-Aviv (IL)

(72) Inventors: Moshe Portnoy, Ramat-Hasharon (IL); Irit Gil-Ad, Herzliya (IL); Avraham Weizman, Tel Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 13/748,861

(22) Filed: Jan. 24, 2013

(65) Prior Publication Data
US 2013/0131048 A1    May 23, 2013

Related U.S. Application Data

(62) Division of application No. 12/447,381, filed as application No. PCT/IL2007/001296 on Oct. 25, 2007, now Pat. No. 8,394,790.

(60) Provisional application No. 60/854,091, filed on Oct. 25, 2006.

(51) Int. Cl.
| A61K 31/551 | (2006.01) |
| C07D 403/04 | (2006.01) |
| C07D 495/04 | (2006.01) |
| A61K 47/48  | (2006.01) |

(52) U.S. Cl.
CPC ............ *C07D 495/04* (2013.01); *C07D 403/04* (2013.01); *A61K 31/551* (2013.01); *A61K 47/48038* (2013.01); *A61K 47/481* (2013.01)
USPC .......................................... 514/220; 540/557

(58) Field of Classification Search
USPC .......................................... 514/220; 540/557
See application file for complete search history.

(56) References Cited

U.S. PATENT DOCUMENTS

| 7,807,828 B2 | 10/2010 | Solomon et al. |
| 7,884,186 B2 * | 2/2011 | Huebert et al. ............... 530/331 |
| 2007/0105836 A1 * | 5/2007 | Pettersson et al. ....... 514/211.13 |

FOREIGN PATENT DOCUMENTS

| WO | WO 2005/019166 A2 | 3/2005 |
| WO | WO 2006/020573 A2 | 2/2006 |
| WO | WO 2007/065036 A2 | 6/2007 |

OTHER PUBLICATIONS

Madsen et al., Development and Evaluation of an Electrochemical Method for Studying Reactive Phase-I Metabolites: Correlation to in Vitro Drug Metabolism, Chemical Research in Toxicology, vol. 20, No. 5, pp. 821-831, Apr. 21, 2007.*
Liu et al., Clozapine is Oxidized by Activated Human Neutrophils to a Reactive Nitrenium Ion that Irreversibly Binds to the Cells, The Journal of Pharmacology and Experimental Therapeutics, vol. 275, No. 3, pp. 1476-1483, Dec. 1995.*
Maggs et al., The Metabolic Formation of Reactive Intermediates from Clozapine, A Drug Associated with Agranulocytosis in Man, The Journal of Pharmacology and Experimental Therapeutics, vol. 275, No. 3, pp. 1463-1475, Dec. 1995.*
Fischer et al., Possible Role of Free Radical Formation in Clozapine (Clozaril)-Induced Agranulocytosis, Molecular Pharmacology, vol. 40, No. 5, pp. 846-853, 1991.*
International Search Report for International Application No. PCT/IL2007/001296, issued Apr. 4, 2008.
Blotnik, Simcha et al., "The Disposition of Valproyl Glycinamide and Valproyl Glycine in Rats," *Pharmaceutical Research*, 1997, pp. 873-878, vol. 14, No. 7.
Scriba, Gerhard K.E. et al., "Synthesis and Anticonvulsant Activity of N-Benzyloxycarbonyl-Amino Acid Prodrugs of Phenytoin," *Journal of Pharmacy and Pharmacology*, 1999, pp. 549-553, vol. 51, No. 5.

* cited by examiner

*Primary Examiner* — Brenda Coleman
(74) *Attorney, Agent, or Firm* — Oliff PLC

(57) ABSTRACT

The invention provides novel compounds and pharmaceutical compositions for the treatment of psychological and/or psychiatric diseases or disorders.

11 Claims, 23 Drawing Sheets

Effect of PGW-7 (12.5, 25, 50 mg/kg, ip) in the Open field test on Distance moved [cm] on BALB/c mice [20min]

Effect of PGW-7 (12.5, 25, 50 mg/kg, ip) in the Open field test on Not moving total duration [%] on BALB/c mice [20 min]

Effect of Compound 1, MK-801 and combination in the Open field test on Rearing frequency Distance moved total [cm] on BALB/c mice Effect of Compound1, MK-801 and combination in the Open field test on in zone total duration (zone 3)

Effect of PGW-7 ( 12.5, 25, 50 mg/kg, ip,-60min), MK-801(0.15 mg/kg,ip,-20 min) and combination in the Open field test on Distance moved [cm] on BALB/c mice [20 min]

PSYCHOTROPIC AGENTS HAVING GLUTAMATE NMDA ACTIVITY

This is a Division of application Ser. No. 12/447,381 filed Jun. 26, 2009, which in turn is a National Phase of Application No. PCT/IL2007/001296, filed Oct. 25, 2007, which claims the benefit of U.S. Provisional Application No. 60/854,091, filed Oct. 25, 2006. The disclosure of the prior applications is hereby incorporated by reference herein in its entirety.

FIELD OF THE INVENTION

The present invention is generally in the field of pharmaceutical compositions and methods for the treatment of psychological and/or psychiatric diseases or disorders.

BACKGROUND OF THE INVENTION

Glutamate is the most abundant excitatory amino acids in the central nervous system (CNS). Glutamate acts through a number of receptors that affect both fast and slow neurotransmission. The fast ionotropic N-methyl-D-aspartate (NMDA), the amino-3-hydroxy-5-methyl-4-isoxazole (AMPA), and the slow metabotropic kainate receptor are a series of G-protein coupled receptors. The ionotropic NMDA receptors are excitatory which has binding sites for glutamate and glycine, and possess an important role in memory and in mood disorders. The metabotropic kainate glutamate receptors (mGluRs) are present at both presynaptic and postsynaptic sites and are considered major targets in the area of neuropharmacology, including schizophrenia, depression, learning, memory, anxiety, seizures, addiction to drugs, neurodegeneration and developmental regulation of synaptic circuits.

The anti-psychotic drugs are widely used in the treatment of central nervous system (CNS) psychotic diseases and disorders, such as schizophrenia. These agents block generally dopamine receptors and are divided into typical and atypical classes; phenothiazines are, for example, typical antipsychotics and clozapine, olanzapine and risperidone are classified as atypical antipsychotics. It is well known in the art that typical neuroleptic agents induce extrapyramidal symptoms, which include rigidity, tremor, bradykinesia (slow movement), and bradyphrenia (slow thought), as well as tardive dyskinesia, acute dystonic reactions and akathasia. Atypical antipsychotics cause minimal extrapyramidal symptoms and thus rarely cause tardive dyskinesias, akathasia or acute dystonic reactions. The administration of atypical antipsychotic agents involves other side effects such as increase of body weight, mood disturbances, sexual disfunction, sedation, orthostatic hypotension, hypersalivation, lowered seizure threshold and, in particular, agranulocytosis.

Schizophrenia is a chronic, debilitating disease with significant morbidity and mortality that often requires antipsychotic pharmacotherapy for life. Current therapy consists of neuroleptics of the typical and the atypical type which share a common anti-dopaminergic activity. In recent years, evidence has been accumulated suggesting that schizophrenia and bipolar disorders are also associated with disturbance in GABA and glutamate transmission in the brain. Recent studies suggest that schizophrenia is associated with NMDA receptor pathology. This hypothesis is based on the experimental finding that agents that block NMDA receptors such as phencyclidine (PCP) and MK-801 induce psychoses similar to that associated with schizophrenia. Post-mortem data in brains of schizophrenic patients showed also a decrease in the expression of several glutamate receptor subtypes including NMDA, AMPA and Kainate in different brain areas. Since hypo function of the NMDA system is considered to have an important role in schizophrenia, and schizophreniform psychosis caused by PCP resembles schizophrenia especially in negative symptoms and cognitive dysfunction, it was suggested that NMDA inhibition would lead to diminished GABAergic tone, which in turn will induce disinhibition of glutamatergic AMPA receptor resulting in excitotoxic neuronal damage and psychosis.

Since direct-acting NMDA agonists, such as glutamate, might be neurotoxic, research focused on assessing the therapeutic activity of partial or full agonists on the glycine (GLY) site of the NMDA receptors. Agents like D-serine and D-cycloserine (DCS) showed in some clinical studies an improvement of mainly primary negative symptoms of schizophrenia when used as adjuvants to conventional neuroleptics such as risperidone and olanzapine. Sarcosine is a glycine transporter 1 inhibitor found efficacious in improving symptoms (negative and positive) of patients with stable chronic schizophrenia. The disadvantage, however, associated in the use of these amino acids lies in the fact that they scarcely penetrate the blood brain barrier (BBB).

Glutamate receptors subtype antagonists, agonists and partial agonists are target of intensive research. The NMDA receptor antagonist memantine was developed for the treatment of Alzheimer's disease. The partial agonist agent D-cycloserine was found to induce some antidepressant and anxiolytic activity in animal models and to improve mood, insomnia and appetite. It is suggested that its anxiolytic effect is related to increased learning and fear extinction. Yet, a significant antidepressant activity of D-cycloserine compared to placebo in men was not observed. Furthermore, agents targeting both the ionotrophic and the metabotrophic receptors of glutamate are under different stages of development for the treatment of anxiety, depression, cognitive and motor disorders.

SUMMARY OF THE INVENTION

The present invention discloses novel Central Nervous System (CNS) active compounds, such as psychotropic agents, having anti-dopaminergic activity and ability to modulate glutamate N-methyl-D-aspartate (NMDA) receptor activity. Such agents are useful in the treatment of schizophrenia and bipolar depression, and in particular have the ability to alter the negative symptoms of schizophrenia. Such novel agents are also useful in altering states of other mood disorders such as depression and anxiety, cognitive deficits, movement disorders and drug addiction.

In one aspect of the present invention, there is provided a CNS active compound (herein a compound of the invention) conjugated to a modulator of the glutamate NMDA receptor. The CNS compound conjugated as recited herein, as known to a person skilled in the art, is a therapeutic agent that acts at a site within the central nervous system, particularly within the brain. CNS-active compounds include CNS depressants, CNS stimulants, and drugs that selectively modify CNS function, such as anticonvulsants, anti-Parkinsonian drugs, opioid and non-opioid analgesics, appetite suppressants, anti-emetics, analgesic-antipyretics, certain stimulants, antidepressants, antimanic agents, antipsychotic agents, sedatives and hypnotics.

Within the scope of the present invention, the CNS-active agents are not limited to agents that act solely within the central nervous system.

In one embodiment, the compound of the invention, or a salt, a prodrug, or a stereoisomer thereof, is of the general formula L-M-V, wherein
L is a CNS active moiety;
M is a linker; and
V is a modulator of the glutamate NMDA receptor.

It should be noted that within the scope of the present invention, the CNS active agent when part of a compound of the invention is referred to as a "CNS active moiety", signifying its conjugation to the linker, M, or the modulator of the glutamate NMDA receptor V.

The compound of the formula L-M-V may be schematically exemplified as shown:

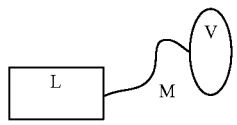

Linker M may be conjugated to the CNS active moiety, L, via any atom of the CNS active moiety. The conjugation to L may be through one or more of the native atoms of the CNS active compound, namely through one or more atoms selected, for example, amongst C, N, S, P, and O, of the CNS active compound (in its unconjugated form), or through a chemically modified part of the CNS active compound, provided that such a modification (necessary for the attachment of the linker M) does not alter or diminish the activity associated with the CNS active compound.

Linker M may be conjugated to the modulator of the glutamate NMDA receptor, V, through any atom of the linker. As the modulator is typically an amino acid or an amino acid derivative, conjugation to the amino acid or amino acid derivative is typically through the α-carbon atom of the amino acid or amino acid derivative, as demonstrated below.

In cases where chemical modification of the CNS active compound and/or the modulator is required to enable bonding of the linker moiety, M, thereto (to either or both L and V), the modification may be any such modification known to a person skilled in the art. Based on the description provided herein, the artisan would know how to chemically modify a CNS active compound for conjugation. For general synthetic methodologies, see for example *Comprehensive Organic Transformations: A Guide to Functional Group Preparations*, Richard C. Larock, $2^{nd}$ Ed., John Wiley & Sons, Inc., 1999.

In some embodiments, the bond between M and L and/or between M and V is non-hydrolysable, namely the linker M does not dissociate from either the CNS active moiety and/or the modulator of the glutamate NMDA receptor, V, under aqueous physiological conditions. In some embodiments, the bonds between M and L and/or M and V are covalent.

In some embodiments, only one of the bonds between M and L or M and V is a non-hydrolizable bond while the other is a hydrolizable bond.

In other embodiments, both the bonds between M and L and between M and V are non-hydrolizable.

As stated above, the CNS active moiety may be any one moiety derived from a CNS active compound selected from the classes typically referred to as CNS depressants, CNS stimulants, and drugs that selectively modify CNS function, such as anticonvulsants, anti-Parkinsonian drugs, opioid and non-opioid analgesics, appetite suppressants, antiemetics, analgesic-antipyretics, stimulants, antidepressants, antimanic agents, antianxiety agents, antipsychotic agents, sedatives and hypnotics.

In some embodiments, the CNS active moiety is selected from an anti-depressant compound, an anti-psychotic compound, an anti-epileptic compound, anti-anxiety and a compound for treating a movement disorder.

In one embodiment, the CNS active moiety is derived from an anti-depressant compound selected amongst anti-unipolar agents and anti-bipolar agents. Non-limiting examples of anti-unipolar agents are fluoxetine, fluvoxamine, desipramine, paroxetine and sertraline.

Non-limiting examples of anti-bipolar agents are remoxipride, alizapride, clozapine, olanzapine and quetiapine.

In another embodiment, the CNS active moiety is derived from an anti-psychotic compound selected from clozapine, olanzapine, quetiapine, loxapine, risperidone, flupenthixol, thioridazine, chlorpromazine, perphenazine, fluphenazine, zuclopenthixol, spiperone, amisulpride, sulpiride, remoxipride and alizapride.

In yet another embodiment, the CNS active moiety is derived from an anti-anxiety compound selected from fluoxetine, fluvoxamine, desipramine, paroxetine and sertraline.

In some other embodiments, the CNS active moiety is derived from a CNS active compound selected amongst monocyclic, bicyclic and tricyclic anti-psychotic agents.

Non-limiting examples of monocyclic agents are amisulpride, sulpiride. Non-limiting examples of bicyclic agents are spiperone, remoxipride, alizapride. Non-limiting examples of tricyclic agents are chlorpromazine, perphenazine, fluphenazine, zuclopenthixol, clozapine, olanzapine, quetiapine, loxapine, flupenthixol and thioridazine.

In certain embodiments, the CNS active moiety is derived from clozapine, olanzapine, or quetiapine.

Within the scope of the present invention, the expression "CNS active moiety derived from" signifies the conjugation of a CNS active compound, as defined and exemplified, to afford a conjugate form of the compound, namely a conjugate moiety having the linker conjugated thereto. For example, a CNS active moiety derived from clozapine is a compound of the invention in which L is clozapine, M is a linker conjugated to clozapine, and V is a modulator conjugated to M.

The linker M may or may not be present.

In some embodiments, where M is absent, L is conjugated directly to V.

In other embodiments, M is present and is typically a linear group conjugating L and Y through one or more atoms on each moiety. The linear group is typically a chain of between 1 and 8 atoms having at least one atom selected from C, N, O and S.

In some embodiments, M is selected from —NH—, —NH$_2^+$—, —O—, —S—, $C_1$-$C_8$-alkylene, $C_3$-$C_8$-cycloalkylene, —CH$_2$—O—CH$_2$—, —(CH$_2$)$_n$—O—(CH$_2$)$_n$—, —(CH$_2$—O)$_n$—, and —(CH$_2$CH$_2$—O)$_n$—, wherein said alkylene and cycloalkylene may optionally be substituted by one or more groups selected from $C_1$-$C_4$ alkyl, $C_2$-$C_4$ alkenyl, and $C_2$-$C_4$ alkynyl, and wherein each of n, independently of each other, is an integer between zero and 3 (i.e., being 0, or 1, or 2, or 3). The alkylene or cycloalkylene may be interrupted by at least one heteroatom selected from N, O and S or by at least one or more double or triple bond.

Non-limiting examples of a linker are —NH—, —O—, —S—, methylene, ethylene, propoylene, isopropylene, isobutylene, sec-butylene, tert-butylene, butylenes, pentylene, isohexylene, hexylene, heptylene, octylene, —(CH$_2$—CH═CH—CH$_2$)—, —(CH═CH$_2$—CH$_2$—CH$_2$)—, —(CH$_2$—CH═CH—CH$_2$—CH$_2$—CH$_2$)—, —(CH$_2$—C≡C—CH$_2$)—, —(C≡C—CH$_2$—CH$_2$)—, —(CH$_2$—NH—CH═CH—CH$_2$)—, —(CH$_2$—NH—CH$_2$—CH$_2$—CH$_2$)—, —(CH$_2$—O—CH$_2$—CH$_2$)—, —(CH$_2$)$_n$—O—(CH$_2$)$_n$—, —CH$_2$—O—CH$_2$—, —(CH$_2$—O)$_n$—, —(CH$_2$CH$_2$—O)$_n$— wherein n is an integer between 0 and 3, and substituted derivatives thereof.

The modulator of the glutamate NMDA receptor, V, is typically an amino acid, or ester, or amide, or alkylated amine of said amino acid. In some embodiments, the amino acids are selected from glycinyl (derived from glycine), sarcosinyl (derived from sarcosine), serinyl (derived from serine) and cysteinyl (derived from cysteine). In other embodiments, the amino acids are esters or amides of glycinyl, sarcosinyl, serinyl and cysteinyl.

In further embodiments, the modulator of the glutamate NMDA receptor is (1S,2S,5R,6S)-2-aminobicyclo[3.1.0] hexane-2,6-dicarboxylate (LY354740) or a derivative thereof.

Non-limiting examples of esters of the above amino acids are $C_1$-$C_6$ esters such as methyl, ethyl, propyl, butyl and hexyl esters of glycinyl, sarcosinyl, and serinyl. The amides may be of $C_2$-$C_6$ acids (of the general formula $C_1$-$C_6$—COOH, wherein the $C_1$-$C_6$ carbon moiety attached to the —COOH, from which the amide is derived, is an alkyl having between 1 and 6 carbon atoms).

It is to be understood that the compounds provided herein may contain one or more chiral centers. Such chiral centers may be of either the (R) or (S) configuration, or may be a mixture thereof. Thus, the compounds provided herein may be enantiomerically pure, or be stereoisomeric or diastereomeric mixtures. In the case of the amino acid moieties constituting the functional moieties of the glutamate NMDA receptor, either the L- or D-form may be present. As used herein, the term "amino acid" refers to α-amino acids which are racemic, or of either the D- or L-configuration.

It is also to be understood that the chiral centers of the compounds provided herein may undergo epimerization in vivo. As such, one of skilled in the art will recognize that administration of a compound in its (R) form is equivalent, for compounds that undergo epimerization in vivo, to administration of the compound in its (S) form.

The term "alkylene" as used herein refers to an alkyldiyl functional group having two free valences carbon atoms, namely an alkyl group substituted at both ends. The expression "$C_1$-$C_8$ alkylene" refers to such an alkyl group having between 1 and 8 carbon atoms. The term "cycloalkylene" similarly refers to a cyclic alkyl being substituted at both ends.

Additionally, as may be known to a person skilled in the art, the term "$C_1$-$C_4$ alkyl" refers to an aliphatic chain of between 1 and 4 carbon atoms, being substituted at one position only. The term "$C_2$-$C_4$ alkenyl" refers to a carbon chain having between 2 and 4 carbon atoms and at least one C—C bond being a double bond. The term "$C_2$-$C_4$ alkynyl" refers to a carbon chain having between 2 and 4 carbon atoms and at least one C—C triple bond.

In certain embodiments of the invention, the CNS active compound is a tricyclic anti-psychotic agent of the general formula (A) and the CNS active moiety is derived therefrom:

Formula (A)

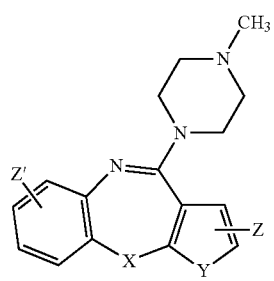

wherein

X is selected from —NH—, —O— and —S—;

Y is selected from —C=C—, —NH—, —O—, and —S—;

Z and Z' are each independently selected from $C_1$-$C_4$ alkyl and halide (I, Br, Cl and F). In some cases, each of the rings substituted by Z or Z' may be substituted by one or more of Z and/or Z'.

In some embodiments, X is —NH— or S and Y is —C=C— or S. In other embodiments, where X is —NH—, Y is —C=C— or —S—. In other embodiments, where X is S, Y is —C=C—.

In further embodiments, Z is a methyl group. In still further embodiments, Z' is a halide.

In further embodiments, the tricyclic compound of formula (A) is selected from olanzapine, quetiapine, and clozapine, the structures of which are shown below and the CNS active moiety is derived from olanzapine, quetiapine, or clozapine:

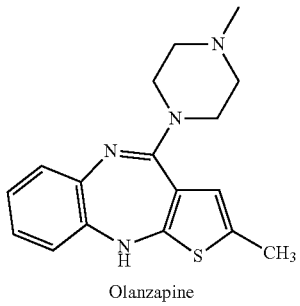

Olanzapine

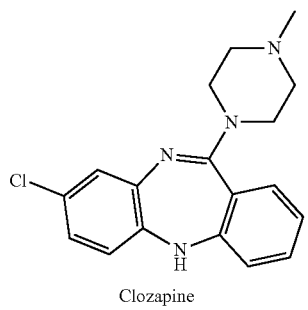

Clozapine

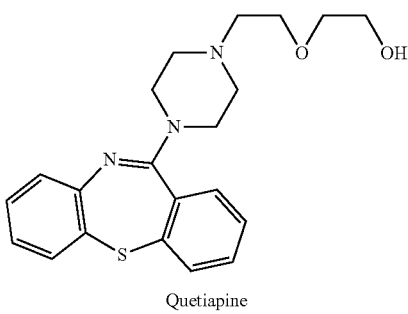

Quetiapine

These compounds may be conjugated to a linker through any one of their carbon or heteroatoms (i.e., S, N or O). As an example, olanzapine may be conjugated to a linker via any of the atoms shown with an arrow:

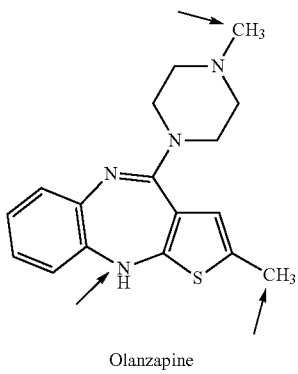 [SMILES: Cc1cc2c(s1)Nc1ccccc1N=C2N1CCN(C)CC1]

Olanzapine

In some embodiments, where the CNS active moiety is derived from olanzapine, the compound of the general formula L-M-V is a compound of formula (I):

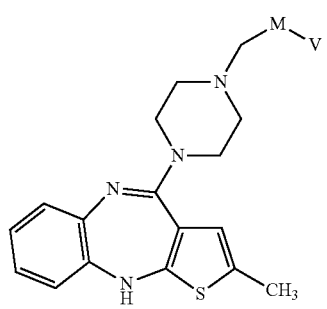

Formula (I)

wherein M and V are as defined above.

In some embodiments, the modulator of the glutamate NMDA receptor, V, is glycinyl, or an ester thereof, and the compound is of the formula (Ia):

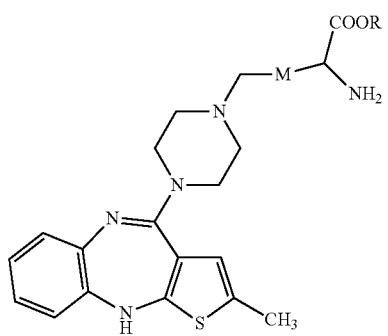

Formula (Ia)

wherein in the compound of general formula (Ia):

M is selected from null, —NH—, —O—, —S—, $C_1$-$C_8$-alkyl, $C_3$-$C_8$-cycloalkyl, —$CH_2$—O—$CH_2$—, —($CH_2$—O)$_n$—, and —($CH_2CH_2$—O)$_n$—, n is an integer between 0 and 3, and R is selected from H and a $C_1$-$C_4$ alkyl.

In some embodiments of formula (Ia), the linker is absent and exemplary compounds of the invention are herein designated Compounds 1 and Compound 2.

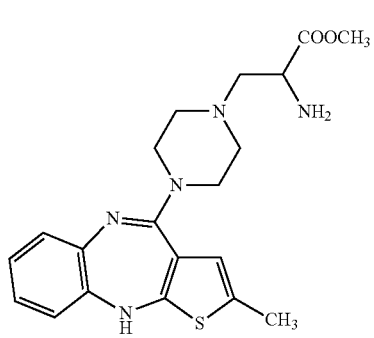

Compound 1

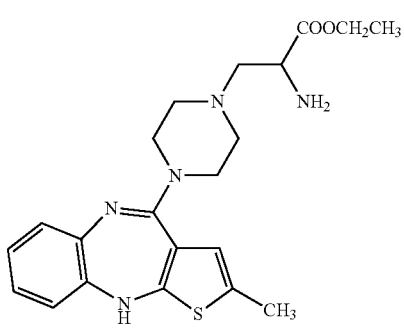

Compound 2

In some other embodiments of formula (Ia), the linker contains at least one heteroatom selected from N, O and S.

In some embodiments, the linker is a $C_1$-$C_5$-alkylene containing at least one heteroatom.

In some further embodiments, the $C_1$-$C_5$-alkylene is interrupted by an O atom and exemplary groups are —$CH_2$—O—$CH_2$—, —($CH_2$—O)$_n$—, and —($CH_2CH_2$—O)$_n$—, wherein n is an integer between 1 and 3 (i.e., 1 or 2 or 3).

Exemplary compounds of such a structure of formula (Ia) are the compounds herein designated as Compound 3 and Compound 4.

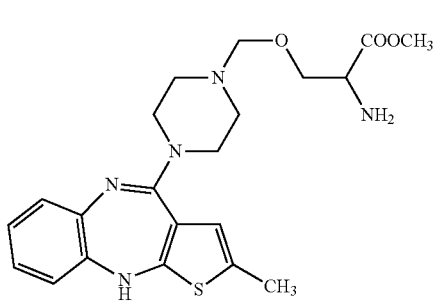

Compound 3

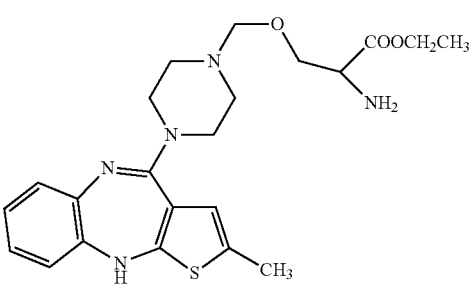

Compound 4

In certain embodiments of general formula (I), the modulator of the glutamate NMDA receptor is sarcosinyl, or an ester thereof or serinyl, or an ester thereof, and the compound is of formula (Ib):

Formula (Ib)

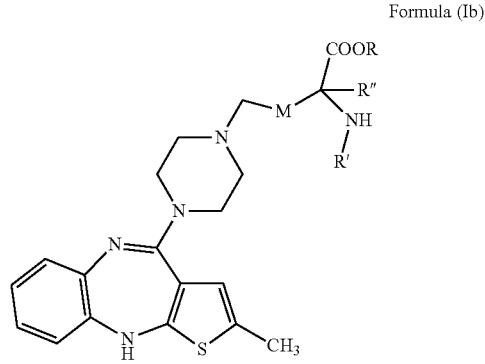

wherein in the compound of formula (Ib):

M is selected from null, —NH—, —O—, —S—, $C_1$-$C_8$-alkyl, $C_3$-$C_8$-cycloalkyl, —CH$_2$—O—CH$_2$—, —(CH$_2$—O)$_n$—, and —(CH$_2$CH$_2$—O)$_n$—, n is an integer between 0 and 3, R and R', independently of each other are selected from H and a $C_1$-$C_4$-alkyl, and R" is selected from H and —CH$_2$OH.

In some embodiments, where R' is a $C_1$-$C_4$-alkyl, R" is H and R is optionally different from H.

In some embodiments, where R' is H, R" is —CH$_2$OH.

In other embodiments, in the compound of formula (Ib), the linker M is absent, R" is H and R' is selected from H and $C_1$-$C_4$-alkyl. Exemplary compounds of the invention are herein designated Compound 5 through Compound 10.

Compound 5

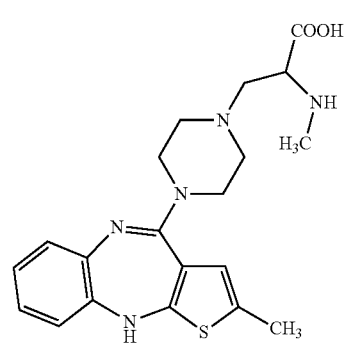

Compound 6

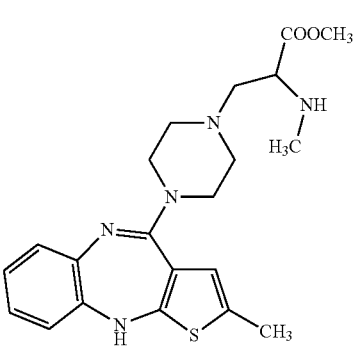

Compound 7

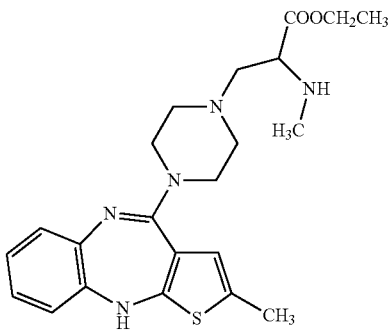

Compound 8

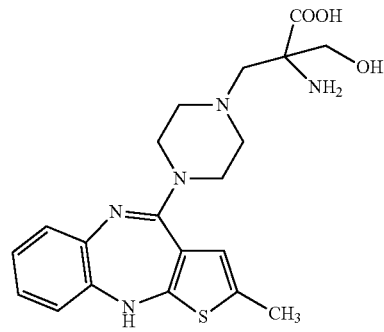

Compound 9

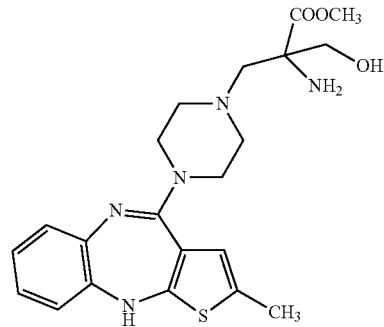

Compound 10

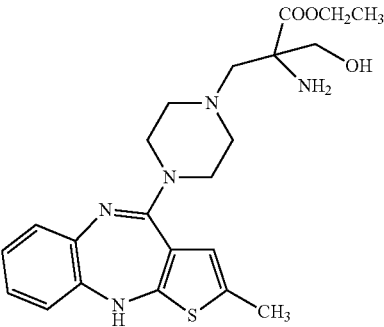

In other embodiments of formula (Ib), the linker, M, is $C_1$-$C_5$-alkylene containing a heteroatom selected from N, O and S.

In some embodiments, the linker is a $C_1$-$C_5$-alkylene interrupted by at least one O atom, such as —CH$_2$—O—CH$_2$, —(CH$_2$—O)$_n$—, and —(CH$_2$CH$_2$—O)$_n$—, wherein n is as defined above. Exemplary compounds are herein designated as Compound 11 through Compound 13.

Compound 11

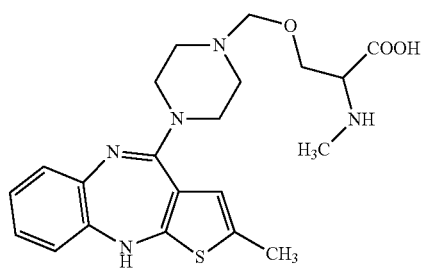

Compound 12

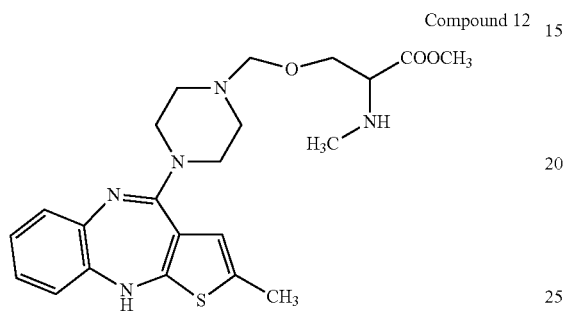

Compound 13

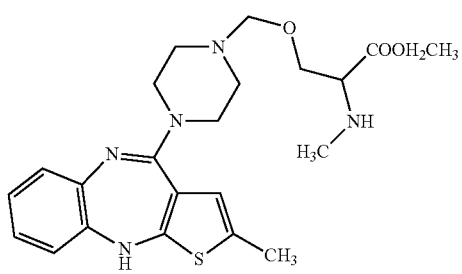

Similarly to Compounds 1 through 13, which are based on olanzapine as the CNS active moiety, compounds of the general formula L-M-V which are based on clozapine and quetiapine have also been prepared. Table 1 lists an exemplary selection of compounds according to the invention. In Table 1, "Ola" stands for olanzapine; "Clo" stands for clozapine; and "Que" stands for quetiapine, each with a point of substitution as shown:

TABLE 1

Compounds of the general formula L-M-V

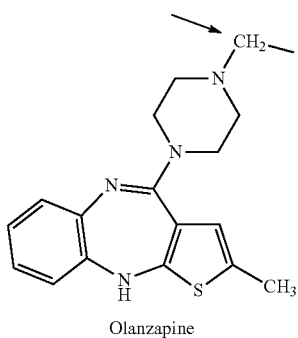

Olanzapine

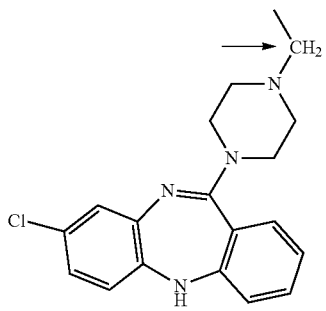

Clozapine

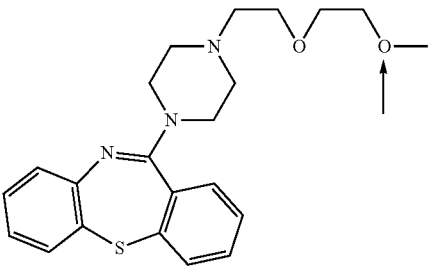

Quetiapine

TABLE 1-continued

| Compound No. | L | M | N |
|---|---|---|---|
| 1 | Ola | absent | —CH(NH$_2$)(COOCH$_3$) |
| 2 | Ola | absent | —CH(NH$_2$)(COOCH$_2$CH$_3$) |
| 3 | Ola | —OCH$_2$— | —CH(NH$_2$)(COOCH$_3$) |
| 4 | Ola | —OCH$_2$— | —CH(NH$_2$)(COOCH$_2$CH$_3$) |
| 5 | Ola | absent | —CH(NHCH$_3$)(COOH) |
| 6 | Ola | absent | —CH(NHCH$_3$)(COOCH$_3$) |
| 7 | Ola | absent | —CH(NHCH$_3$)(COOCH$_2$CH$_3$) |
| 8 | Ola | absent | —C(NH$_2$)(CH$_2$OH)(COOH) |
| 9 | Ola | absent | —C(NH$_2$)(CH$_2$OH)(COOCH$_3$) |
| 10 | Ola | absent | —C(NH$_2$)(CH$_2$OH)(COOCH$_2$CH$_3$) |
| 11 | Ola | —OCH$_2$— | —CH(NHCH$_3$)(COOH) |
| 12 | Ola | —OCH$_2$— | —CH(NHCH$_3$)(COOCH$_3$) |
| 13 | Ola | —OCH$_2$— | —CH(NHCH$_3$)(COOCH$_2$CH$_3$) |
| 14 | Ola | —CH$_2$CH$_2$OCH$_2$— | —CH(NH$_2$)(COOCH$_3$) |
| 15 | Ola | —CH$_2$CH$_2$OCH$_2$— | —CH(NH$_2$)(COOCH$_2$CH$_3$) |
| 16 | Ola | —CH$_2$CH$_2$OCH$_2$— | —CH(NHCH$_3$)(COOCH$_3$) |
| 17 | Ola | —CH$_2$CH$_2$OCH$_2$— | —CH(NHCH$_3$)(COOCH$_2$CH$_3$) |
| 18 | Clo | absent | —CH(NH$_2$)(COOCH$_3$) |
| 19 | Clo | absent | —CH(NH$_2$)(COOCH$_2$CH$_3$) |
| 20 | Clo | —OCH$_2$— | —CH(NH$_2$)(COOCH$_3$) |
| 21 | Clo | —OCH$_2$— | —CH(NH$_2$)(COOCH$_2$CH$_3$) |
| 22 | Clo | absent | —CH(NHCH$_3$)(COOH) |
| 23 | Clo | absent | —CH(NHCH$_3$)(COOCH$_3$) |
| 24 | Clo | absent | —CH(NHCH$_3$)(COOCH$_2$CH$_3$) |
| 25 | Clo | absent | —C(NH$_2$)(CH$_2$OH)(COOH) |
| 26 | Clo | absent | —C(NH$_2$)(CH$_2$OH)(COOCH$_3$) |
| 27 | Clo | absent | —C(NH$_2$)(CH$_2$OH)(COOCH$_2$CH$_3$) |
| 28 | Clo | —OCH$_2$— | —CH(NHCH$_3$)(COOH) |
| 29 | Clo | —OCH$_2$— | —CH(NHCH$_3$)(COOCH$_3$) |
| 30 | Clo | —OCH$_2$— | —CH(NHCH$_3$)(COOCH$_2$CH$_3$) |
| 31 | Clo | —CH$_2$CH$_2$OCH$_2$— | —CH(NH$_2$)(COOCH$_3$) |
| 32 | Clo | —CH$_2$CH$_2$OCH$_2$— | —CH(NH$_2$)(COOCH$_2$CH$_3$) |
| 33 | Clo | —CH$_2$CH$_2$OCH$_2$— | —CH(NHCH$_3$)(COOCH$_3$) |
| 34 | Clo | —CH$_2$CH$_2$OCH$_2$— | —CH(NHCH$_3$)(COOCH$_2$CH$_3$) |
| 35 | Que | absent | —CH(NH$_2$)(COOCH$_3$) |
| 36 | Que | absent | —CH(NH$_2$)(COOCH$_2$CH$_3$) |
| 37 | Que | —CH$_2$— | —CH(NH$_2$)(COOCH$_3$) |
| 38 | Que | —CH$_2$— | —CH(NH$_2$)(COOCH$_2$CH$_3$) |
| 39 | Que | absent | —CH(NHCH$_3$)(COOH) |
| 40 | Que | absent | —CH(NHCH$_3$)(COOCH$_3$) |
| 41 | Que | absent | —CH(NHCH$_3$)(COOCH$_2$CH$_3$) |
| 42 | Que | absent | —C(NH$_2$)(CH$_2$OH)(COOH) |
| 43 | Que | absent | —C(NH$_2$)(CH$_2$OH)(COOCH$_3$) |

TABLE 1-continued

| 44 | Que | absent | —C(NH$_2$)(CH$_2$OH)(COOCH$_2$CH$_3$) |
| --- | --- | --- | --- |
| 45 | Que | —CH$_2$— | —CH(NHCH$_3$)(COOH) |
| 46 | Que | —CH$_2$— | —CH(NHCH$_3$)(COOCH$_3$) |
| 47 | Que | —CH$_2$— | —CH(NHCH$_3$)(COOCH$_2$CH$_3$) |
| 48 | Que | —CH$_2$— | —C(NH$_2$)(CH$_2$OH)(COOH) |
| 49 | Que | —CH$_2$— | —C(NH$_2$)(CH$_2$OH)(COOCH$_3$) |
| 50 | Que | —CH$_2$— | —C(NH$_2$)(CH$_2$OH)(COOCH$_2$CH$_3$) |
| 51 | Que | —CH$_2$CH$_2$OCH$_2$— | —CH(NH$_2$)(COOCH$_3$) |
| 52 | Que | —CH$_2$CH$_2$OCH$_2$— | —CH(NH$_2$)(COOCH$_2$CH$_3$) |
| 53 | Que | —CH$_2$CH$_2$OCH$_2$— | —CH(NHCH$_3$)(COOCH$_3$) |
| 54 | Que | —CH$_2$CH$_2$OCH$_2$— | —CH(NHCH$_3$)(COOCH$_2$CH$_3$) |

The present invention thus also provides any one of Compounds 1 through 54 listed in Table 1, a salt thereof, a prodrug thereof, and a stereoisomer thereof.

The present invention further encompasses active compounds which are based on mono- and bicyclic antipsychotic agents such amisulpride, sulpiride, spiperone, remoxipride, and alizapride. Such compounds may be utilized as the CNS active moiety, L, in the general formula L-M-V.

For example, the monocyclic anti-psychotic agent amisulpride may be conjugated to a linker at any one of the positions (others are also possible) shown with an arrow:

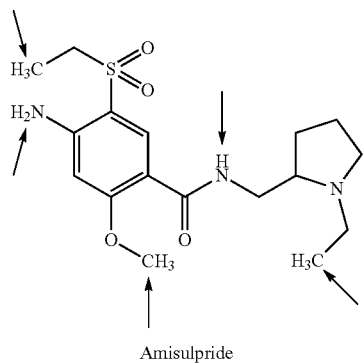 [SMILES: CCN1CCCC1CNC(=O)c1cc(S(=O)(=O)CC)c(N)cc1OC]

Amisulpride

Similarly, alizapride, a bicyclic anti-psychotic, may be modified at the shown positions:

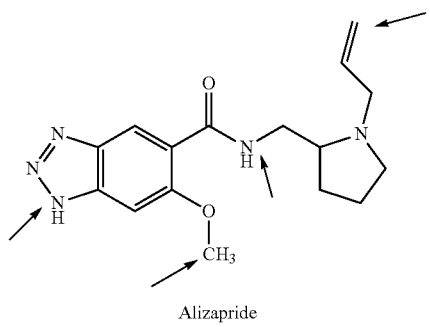 [SMILES: C=CCN1CCCC1CNC(=O)c1cc2nn[nH]c2cc1OC]

Alizapride

The compounds of the invention may be prepared following total synthesis from commercially available starting materials or intermediates. As demonstrated below, olanzapine derivatives were prepared step-wise from substituted thiophene. The synthesis of clozapine proceeded step-wise from a substituted benzene. Once the backbone of the active moiety was prepared, substitution with an appropriate group, constituting the linker and/or the modulator of the glutamate NMDA receptor, was possible.

The quetiapine derivatives were prepared via total-synthesis or alternatively via direct alkylation of the free hydroxyl group of the quetiapine skeleton.

Thus, in another aspect of the present invention, there is provided a method for the preparation of a compound of general formula L-M-V, said method comprising:

(a) providing a reactive precursor of a CNS active moiety, L;

(b) reacting said precursor under appropriate conditions with (i) a derivative of a linker, M, and/or
(ii) a derivative of a the modulator of the glutamate NMDA receptor, V, or
(iii) a pre-synthesized product of a linker and a modulator of the glutamate NMDA receptor having the formula -M-V;

whereby under the reaction conditions said reactive precursor of a CNS active moiety reacts with one of (i)-(iii) to afford, respectively, (1) a CNS active moiety substituted with a linker, M, i.e., having the general formula L-M; or
(2) a CNS active moiety substituted with a modulator of the glutamate NMDA receptor modulator, V, i.e., having the general formula L-V (M being absent); or a CNS active moiety substituted with -M-V (in case steps (i) and (ii) are sequentially followed); or
(3) a CNS active moiety substituted with a modulator of the glutamate NMDA receptor modulator, V, through a linker, M, i.e., having the general formula L-M-V.

Where the intermediate is a precursor of L-M-V, being, for example, of the general structure L-M, the intermediate may be further reacted with an appropriate precursor of the modulator of the glutamate NMDA receptor to afford a compound of the general structure L-M-V.

The reactive precursor of a CNS active moiety, L, is a precursor of the CNS active moiety which may be modified, by methods known in the art, to afford a CNS active moiety conjugated to a linker. The precursor may be one having a free amine group, an alcohol, a thiol, an aldehyde, a ketone, a carboxylic acid or an active carbon group, through which conjugation may take place. The conjugation of the moiety to the linker may take place, depending on the specific reaction conditions employed, under such experimental conditions as would be known to a person skilled in the art, to afford one or more of the following: high yield, selectivity, preference to a single isomer, etc.

The synthesis of specific isomers can be carried out employing methods within the knowledge of one skilled in the art, for example, stereochemically controlled synthesis using chiral synthons or chiral reagents.

The compounds of the invention typically contain at least one basic atom or substituent, and thus are capable of forming a wide variety of different salts with various inorganic and organic acids. Although such salts must be pharmaceutically acceptable for administration to animals (human and non-human), it is often desirable in practice to initially isolate the base compounds from the reaction mixture as other non-acceptable salts, such as perchlorates, picolinates, picrates, or the like, and then convert them to the free base compound by treatment with an alkaline reagent, as known to a person skilled in the art. Subsequently, the free base forms may be converted to the pharmaceutically acceptable acid addition salts.

The acid addition salts of the compounds of this invention are readily prepared by treating the compounds with equivalent amounts of a chosen mineral or organic acid in an aqueous solvent or in a suitable organic solvent, such as methanol or ethanol. The desired solid salt may then be readily obtained by, e.g., evaporation of the solvent.

The pharmaceutically acceptable acid forms of the compounds of the invention, are obtained from non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, and p-toluenesulfonate.

Certain compounds of the present invention have at least one acidic group and are thus capable of forming base salts with various pharmaceutically acceptable cations. Examples of such salts include the alkali metal or alkaline-earth metal salts and, particularly, the sodium and potassium salts.

The chemical bases which are used as reagents to prepare the pharmaceutically acceptable base salts of compounds of the present invention are those which form non-toxic base salts with the herein described acidic derivatives. These particular non-toxic base salts include those derived form such pharmaceutically acceptable cations as sodium, potassium, calcium and magnesium, etc. These salts can easily be prepared by treating the compounds of the invention having at least one acidic group with an aqueous solution containing the desired pharmaceutically acceptable cation, and then evaporating the resulting solution to dryness, in some embodiments under reduced pressure. Typically, stoichiometric quantities of reagents are preferably employed in order to ensure completeness of reaction and maximum production of yields of the desired final product.

Compounds of the invention having both acidic and basic groups may also be obtained as internal salts (Zwitter ions).

The present invention also relates to prodrug derivatives of the compounds of the invention. As known to the person skilled in the art, the term "prodrug" refers to pharmacologically inactive precursors of a drug that may be converted into its therapeutically active form under physiological conditions in vivo, for example, when they undergo solvolysis, or enzymatic degradation in blood, or in cells, (See as background reference: *The Organic Chemistry of Drug Design and Drug Action*, Academic Press, San Diego, Calif., 1992).

Within the scope of the invention, the term also encompasses any covalently bonded carriers, which release the active compound in vivo when administered to an animal. Prodrug modifications of a compound often offer advantages of solubility, bioavailability, absorption, tissue compatibility, tissue distribution, or delayed release in the mammalian organism. While the prodrug derivatives of compounds of the invention have groups cleavable under metabolic conditions, for example, pharmaceutically acceptable esters, or amides, it is to be understood that such cleaving does not refer to cleaving of a bond between moieties L and M and/or V and M in the general formula L-M-V. The cleavable groups being different from L, M and V can be cleaved enzymatically or non-enzymatically, or hydrolytically to the free hydroxy, carboy, or amino group of the active parent compound.

The prodrug may also be a reduced form, which is oxidized in vivo to the therapeutic compound, for example, an alcohol to a carboxylic acid.

Thus, the present invention provides compounds, salts thereof (being pharmaceutically acceptable or unacceptable), internal salts thereof, hydrates thereof, polymorphs thereof, prodrugs thereof and mixtures of any one form thereof.

Pure compounds may be obtained following methods of purification as known in the art. Where the reaction product is a mixture of isomers, specific isomers may be separated by means of classical separation techniques, such as chromatographic or crystallization methods, or by other methods known in the art, such as through formation of diastereomeric salts, for example by salt formation with an enantiomerically pure chiral acid, or by means of chromatography, for example by using chromatographic materials modified with chiral ligands.

The compounds of the invention, as shown herein are modulators of the glutamate NMDA receptor. Within the scope of the present application, the term "modulator" refers to the ability of compounds of the invention to affect (alter) the activity of the glutamate NMDA receptor. The receptor may be over or under activated in response to treatment with one or more of the compounds of the invention. The over- or under-activation of the receptor may be determined by e.g., a functional assay or other in vitro, in vivo, and/or ex-vivo tests such as those demonstrated hereinbelow or such as those known to a person skilled in the art. Thus, in some embodiments, the compounds of the invention are agonists, namely having the ability to activate the glutamate NMDA receptor, or partial agonists, namely only partially activating the receptor. In some other embodiments, the compounds are antagonists, namely having the ability to block or arrest the activity of the glutamate NMDA receptor, or partial antagonist.

In another aspect, the present invention provides the use of at least one compound (or a salt, prodrug, or a stereoisomer thereof) according to the invention for the preparation of a composition. In some embodiments, the composition of the invention is a pharmaceutical composition, comprising also at least one pharmaceutically acceptable carrier, diluent or excipient.

The pharmaceutical composition of the invention may comprise one or more compounds according to the invention. Where the composition comprises two or more compounds, the compounds may be compounds of different classes (e.g., one compound being a tricyclic psychotropic and the other an antidepressant), the compounds may be salt forms of the same compound (e.g., one compound being a sodium salt of Compound 1 and the other a potassium salt of Compound 1), different compounds in different or same form (e.g., one may be a salt and the other may be an ester), in different or same concentrations, etc.

The choice of carrier will be determined in part by the particular compound, as well as by the particular method used to administer the composition comprising it. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions.

Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent.

Capsule forms can be of the ordinary hard- or soft-shelled gelatin type containing, for example, surfactants, lubricants, and inert fillers, such as lactose, sucrose, calcium phosphate, and cornstarch.

Tablet forms can include one or more of lactose, sucrose, mannitol, corn starch, potato starch, alginic acid, microcrystalline cellulose, acacia, gelatin, guar gum, colloidal silicon dioxide, croscarmellose sodiumk talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers.

Lozenge forms can comprise a compound of the invention in a flavor, usually sucrose and acacia or tragacanth, as well as pastilles comprising the active ingredient in an inert base, such as gelatin and glycerin, or sucrose and acacia, emulsions, gels, and the like containing, in addition to a compound of the invention, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

The parenteral formulations will typically contain from about 0.5 to about 25% by weight of the compound of the invention in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986).

The compositions of the invention may comprise at least one compound or a pharmaceutically acceptable salt or derivative thereof and in addition comprise a carrier. Additionally, the composition may comprise at least one drug selected from CNS depressants, CNS stimulants, and drugs that selectively modify CNS function, such as anticonvulsants, anti-Parkinsonian drugs, opioid and non-opioid analgesics, appetite suppressants, antiemetics, analgesic-antipyretics, certain stimulants, antidepressants, antimanic agents, antipsychotic agents, sedatives and hypnotics.

The pharmaceutical compositions of the invention may be administered to a subject, a human or non-human, via any of the administration routes disclosed hereinbefore. The pharmaceutical compositions may be used in a treatment regime of a disease or disorder of choice, as known to a medical practitioner. In some embodiments, the disease or disorder is a psychological or psychiatric disease or disorder.

Thus, the present invention also provides a use of a compound according to the invention in the treatment of a disease or disorder.

The invention further provides a method of treating a disease or disorder comprising administering to a subject in need thereof a compound or a composition according to the present invention.

In some embodiments, said disease or disorder is a psychiatric disease or disorder. In some other embodiments, said disease or disorder is associated with modulation of the activity of the glutamate NMDA receptor. Non-limiting examples of such diseases and disorders are diseases and disorders of the CNS, such as psychotic disorders, anxiety disorders, dissociative disorder, personality disorders, mood disorders, effective disorder, neurodegenerative disorders, convulsive disorders, boarder line disorders and mental diseases and disorders.

In other embodiments, the disease or disorder is selected from Schizophrenia, bipolar disorders (and maintenance for bipolarity), psychotic depression, delussional disorders, conduct disorders, psychosis-induced dementia, organic psychosis, mood disorders, Torte's syndrome, depression, post-traumatic stress disorder, anxiety, panic disorder and Alzheimer's disease.

The invention further provides a method of modulating the activity of the glutamate NMDA receptor, said method comprising contacting a tissue (e.g., a CNS tissue) expressing said glutamate NMDA receptor with at least one compound or a composition according to the invention. The tissue being contacted with the at least one compound or composition according to the invention may be a tissue extracted or removed from the body of the animal (ex vivo) or a tissue in the body of the animal (in vivo).

In some embodiments, said activity is enhanced. In some other embodiments, said activity is decreased.

Also provided by the present invention is a method for modulating one or more biological and/or pharmacological pathways, whereby said modulation ensues the treatment of an at least one psychological and/or psychiatric disease or disorder or the preventing of such a disease or disorder, said method comprising administering to a subject an effective amount of a compound or a composition according to the present invention.

As used herein, the term "effective amount" refers to an amount of a compound of the invention, or a composition comprising thereof which is effective in treating at least one disease or disorder as defined. The amount must be effective to achieve the desired therapeutic effect as described, i.e., of the activity of the glutamate NMDA receptor, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half-life in the body, on undesired side effects, if any, on factors such as age and gender, etc.

The term "treatment" or any lingual variation thereof, as used herein, refers to the administering of a therapeutic amount of the compound of the invention or a composition comprising thereof which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1A shows the effect on distance moved; FIG. 1B shows the effect ion velocity; FIG. 1C shows the effect on rearing frequency; and FIG. 1D shows the duration of the "not moving" periods.

FIG. 2A shows the effect on distance moved; FIG. 2B shows the effect on velocity mean; FIG. 2C shows the effect on rearing frequency; and FIG. 2D shows the total duration of the "not moving" periods.

FIG. 3A shows the effect on the distance moved; FIG. 3B shows the effect on velocity; and FIG. 3C shows the effect on number of rearings.

FIG. 4A shows the effect on the distance moved; FIG. 4B shows the effect on the total duration of "not moving" periods and FIG. 4C shows the effect on the rearing frequency.

FIG. 9A shows the distance moved total; FIG. 9B shows the velocity mean; FIG. 9C shows the effect of Compound 1, MK-801 and a combination thereof on in zone frequency; and FIG. 9D shows the effect of Compound 1, MK-801 and a combination thereof on in zone total duration.

FIG. 10A shows effect of Compound 3, MK-801, and a combination thereof on distance moved; FIG. 10B shows the effect of Compound 3, MK-801, and a combination thereof on "not moving" total duration; FIG. 10C shows the effect of Compound 3, MK-801, and a combination thereof on in-zone frequency (zone 3); and FIG. 10D shows the effect of Compound 3, MK-801, and a combination thereof on in-zone total duration.

FIG. 15E shows the effect of Compound 6 (PGW-5) in the elevated plus maze test.

DETAILED DESCRIPTION OF THE INVENTION

A. Synthesis of Novel Compounds

Figure 1A:
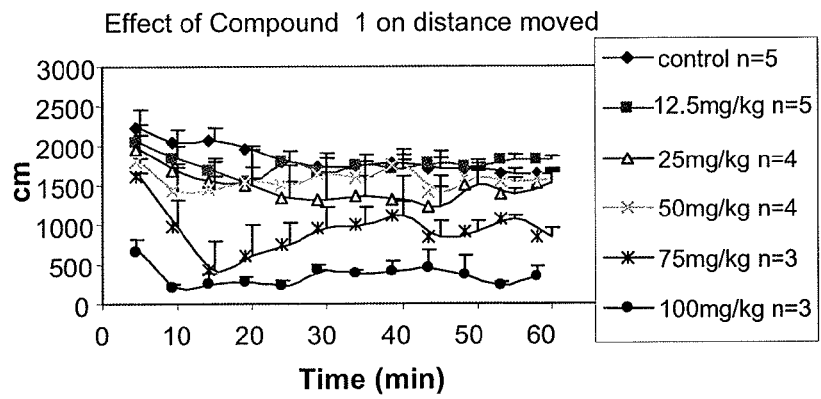
FIGS. 1A-D show the open filed results following i.p. administration of Compound 1 at 12.5, 25, 50, 75 and 100 mg/kg (each point is the mean+/−SEM of 3-5 determinations).
Figure 1B:
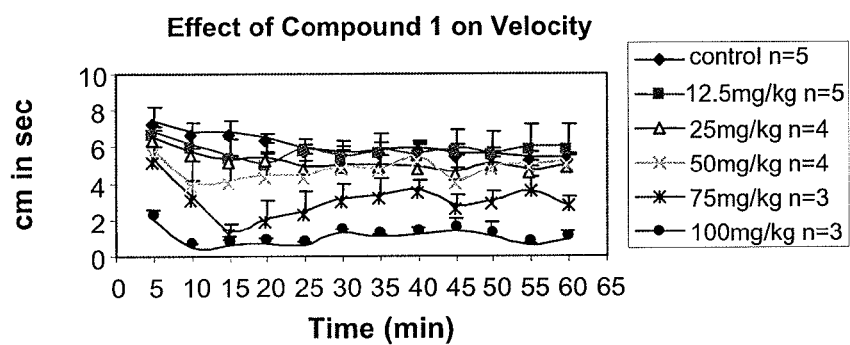
Figure 1C:
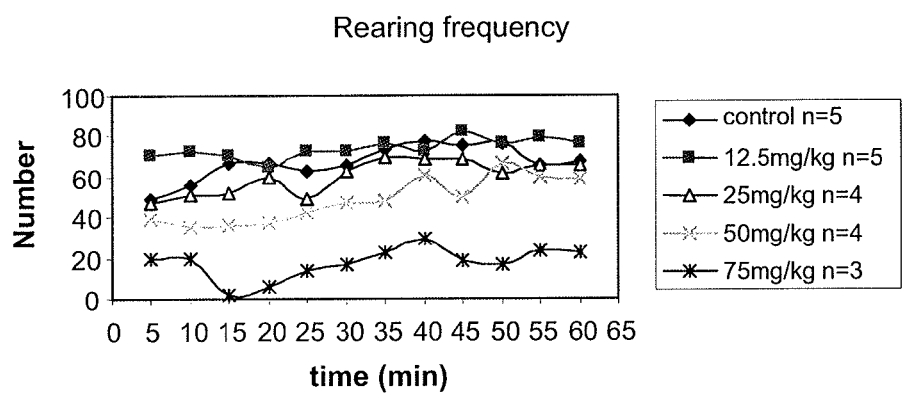
Figure 1D:
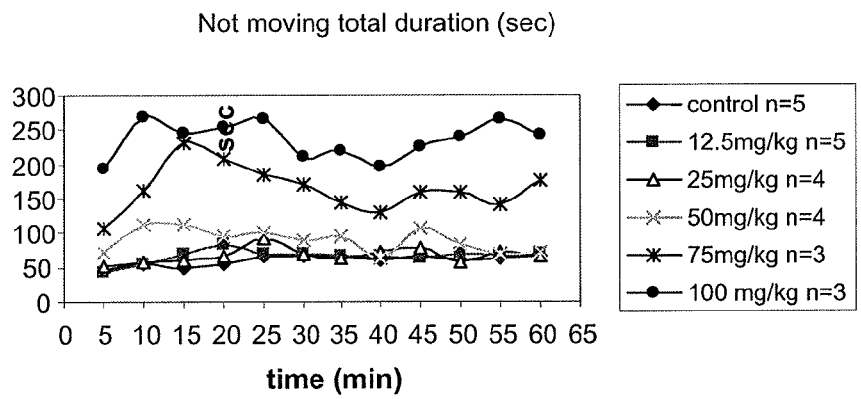
Figure 2A:
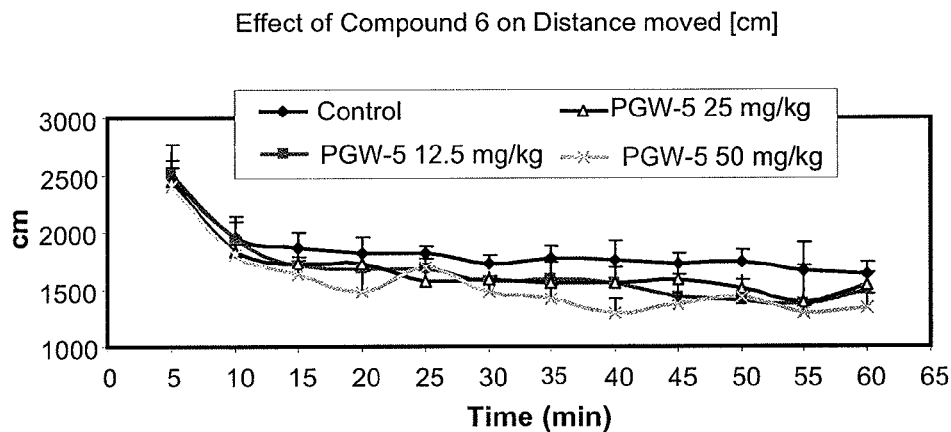
FIGS. 2A-D show (each point is the mean+/−SEM of 6 determinations) the dose-dependent effect of Compound 6 (PGW-5) on the motility of mice.
Figure 2B:
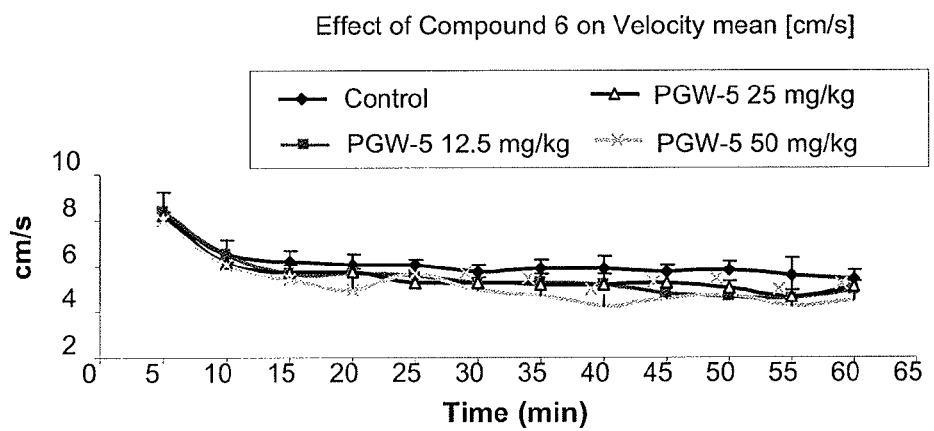
Figure 2C:
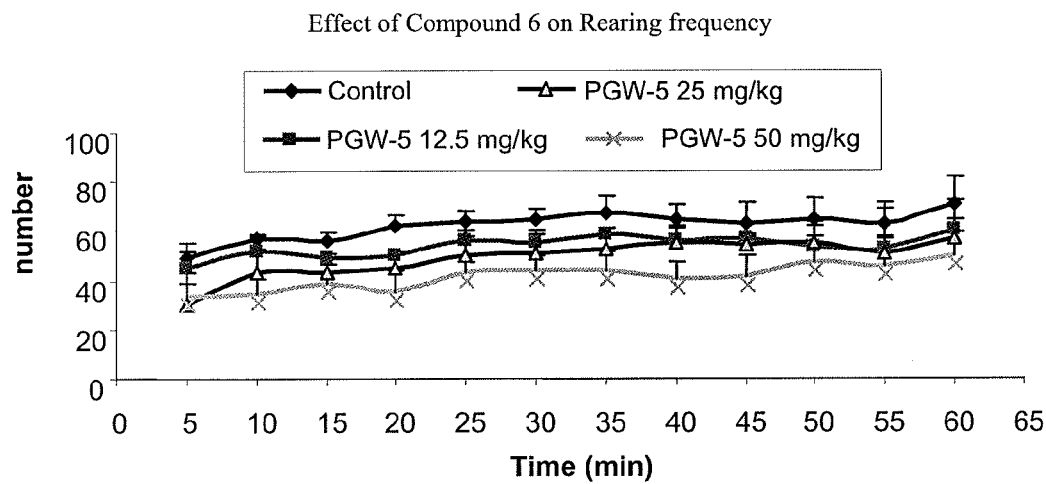
Figure 2D:
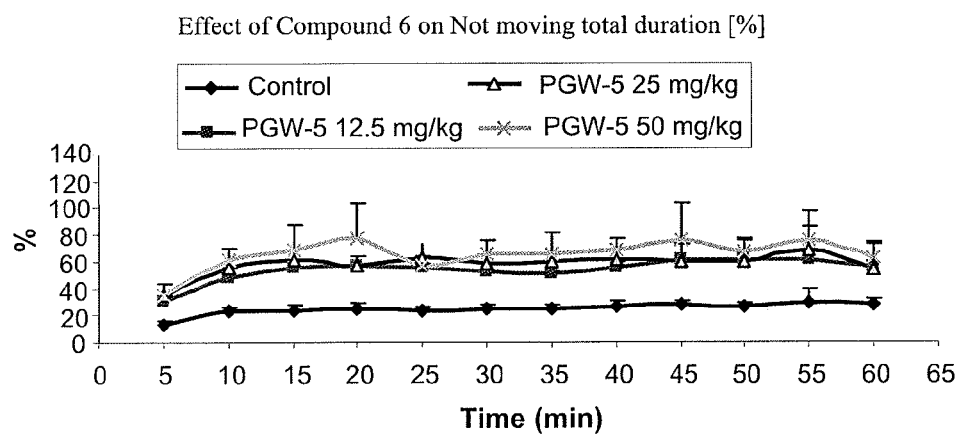

The compounds of the invention may be prepared according to a variety of procedures, as disclosed and exemplified herein. One general way to prepare the compounds of the general formula (A), substituted with the appropriate amino acid, e.g., glycinyl, serinyl or sarcosinyl moieties directly or through a linker, as shown in the specific structures herein, is to first prepare the demethylated derivatives of the parent CNS-active agents (e.g. des-Me-olanzapine, des-Me-clozapine). These can be prepared by coupling two ortho-disubstituted aromatics: one bearing a nitro group in an ortho position to a good leaving group (e.g., fluoride, chloride), while another is an ortho-cyano aromatic amine, phenol or thiophenol. The coupling (for example through an aromatic nucleophilic substitution) forms a nitro cyano-diarylamine, nitro cyano-diarylether, or nitro cyano-diarylthioether. In the next stage, the nitro group is reduced to amine with a simultaneous central diazepine ring closure. The formed tricyclic amidine reacts with piperazine, forming the des-Me form of the L fragment of the target compound, as disclosed and exemplified herein.

The piperazine secondary amine of this intermediate can be further reacted with a β-iodo-alanine, or dehydroalanine derivative (where the linker moiety is absent) or with O-iodoalkyl serine derivatives (where the linker moiety is present). The amine of the amino acid moiety may be protected utilizing any protecting groups known to the person skilled in the art. Typically, in the following examples, the amine was protected with the Boc-protecting group. Deprotection at the final step with an acid such as HCl, afforded the desired active compound in the trihydrochloride salt form.

It should be noted that the following examples are non-limiting in nature and are presented for the full understanding of the invention. The synthetic procedures provided may be varied mutatis mutandis and other novel compounds of the general formulas disclosed herein may be prepared.

Synthesis of Compound 1

(1) Synthesis of
2-Amino-5-methyl-3-thiophenecarbonitrile (A)

For a general synthesis see He, X.; Griesser, U. J.; Stowell, J. G.; Borchrdt, T. B.; Byrn, S. R. *J. Pharm. Sci.* 2001, 90, 371.

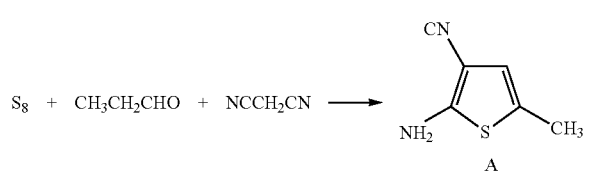

Sulfur ($S_8$, 0.9 g, 0.0 27 mmol), propionalaldehyde (2 ml, 0.027 mmol) and DMF (6 ml) were transferred to a three-necked round-bottomed flask equipped with a dropping funnel and condenser. The resulting mixture was cooled to 0° C., and triethylamine (2.3 ml) was added in a dropwise manner via the dropping funnel. The resulting dark solution was then warmed to room temperature over a period of 1 h. A solution of malononitrile (1.71 ml, 1.8 g, 0.027 mmol) in DMF (3.2 ml) was transferred to the addition funnel and added in a dropwise manner. The resulting brownish mixture was stirred overnight at room temperature. Then the mixture was poured over 80 ml of ice and water to yield an orange precipitate. The solid A was filtered, washed with chilled water, and dried in vacuo; yield 78%.

$^1$H NMR (200 MHz, $CDCl_3$): δ 6.35 (s, 1H), 4.15 (br s, 2H), 2.27 (s, 3H). $^{13}$C NMR (50 MHz, $CDCl_3$): δ 160.9, 146.3, 124.6, 122.0, 115.7, 14.9.

(2) Synthesis of 2-(2-nitroanilido)-5-methyl-3-thiophenecarbonitrile (B)

For a general synthesis see He, X.; Griesser, U. J.; Stowell, J. G.; Borchrdt, T. B.; Byrn, S. R. *J. Pharm. Sci.* 2001, 90, 371.

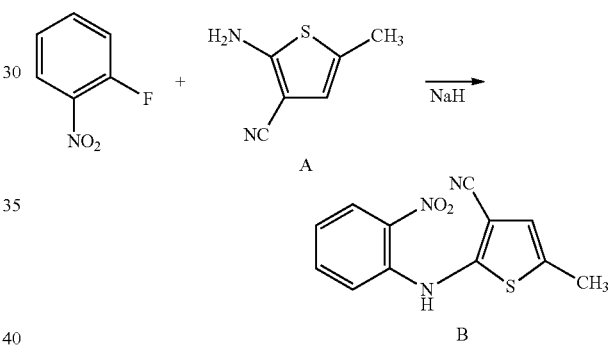

To NaH (3 equivalents, from 55% suspension in oil, rendered oil-free by washing with hexane) was added 1 ml of dry THF. 2-amino-5-methyl-3-thiophenecarbonitrile (A, as prepared above, 0.5 g, 3.6 mmol) and 4-fluoro-3-nitotoluene (0.51 g, 3.6 mmol) were dissolved in dry THF (1.5 ml) and added in a dropwise manner to the suspension while the temperature was maintained below 30° C. The reaction mixture was allowed to stir overnight under $N_2$ purge. The mixture was then poured into 11 ml of ice-water mixture, neutralized with concentrated HCl, and extracted with 36 ml of DCM. The DCM solution was dried over $MgSO_4$ and evaporated to dryness. The residue was purified by flash chromatography on silica gel (elution with 1:9 EtOAc/Hexanes) to give compound B (yield 60%).

$^1$H NMR (200 MHz, $CDCl_3$): δ 9.61 (br s, 1H), 8.25 (dd, J=8.5 Hz, J=1.5 Hz, 1H), 7.52 (dt, J=7.8 Hz, J=1.4 Hz, 1H), 7.19 (dd, J=8.5 Hz, J=1.1 Hz, 1H), 6.97 (dt, J=7.8 Hz, J=1.2 Hz, 1H), 6.78 (d, J=1.1 Hz, 1H), 2.48 (s, 3H).

(3) Synthesis of 4-amino-2-methyl-10H-thieno[2,3-b][1,5]benzodiazepine, hydrochloride salt (C)

For a general synthesis see Chakrabarti, J. K.; Hotten, T. M.; Pullar, I. A.; Steggles, D. J. *J. Med. Chem.* 1989, 32, 2375.

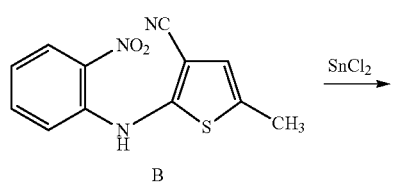

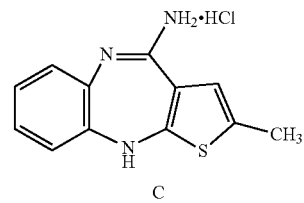

To a slurry of B (100 mg, 0.4 mmol) in ethanol (1 ml) was added tin(II)-chloride-dihydrate (260 mg, 1.16 mmol) in concentrated HCl (1 ml), the solution was heated to reflux for 3 h and cooled overnight, and the solid C was filtered, washed with chilled DCM, and dried in vacuo; yield 95%.

$^1$H NMR (200 MHz, DMSO-$d_6$): δ 11.05 (s, 1H), 9.53 (s, 1H), 9.08 (br s, 1H), 8.82 (br s, 1H), 6.80-7.14 (m, 4H), 6.78 (s, 1H), 2.23 (s, 3H).

(4) Synthesis of 2-methyl-4-(1-piperazinyl)-10H-thieno[2,3-b][1,5]benzo diazepine (D)

For a general synthesis, see Chakrabarti, J. K.; Hotten, T. M.; Pullar, I. A.; Steggles, D. J. *J. Med. Chem.* 1989, 32, 2375.

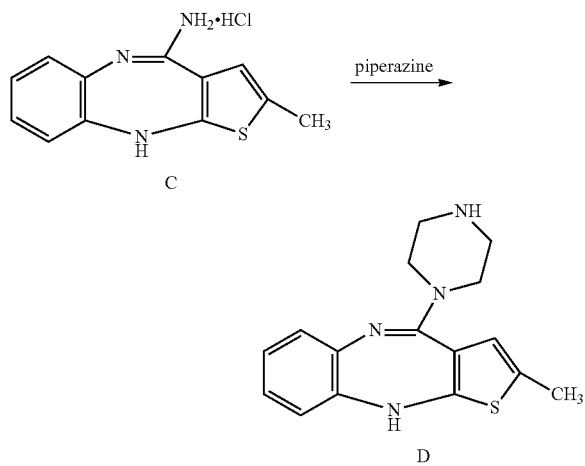

Starting material C (prepared according to the above, 140 mg, 0.53 mmol) was added to a mixture of dry dimethyl sulfoxide (1 ml), dry toluene (1 ml), and piperazine (140 mg, 1.6 mmol). The stirred solution was then heated at 125° C. under nitrogen for 5 h and cooled to room temperature. Then distilled water (2 ml) was added, while the temperature is kept below 25° C. After stirring at 5° C. for 30 minute, the suspension was cooled overnight and the solid D was filtered, washed with chilled water, and dried at 70° C. under reduced pressure; yield 69%.

$^1$H NMR (200 MHz, CDCl$_3$): δ 6.80-7.06 (m, 3H), 6.60 (dd, J=7.4 Hz, J=1.3 Hz, 1H), 6.30 (d, J=0.8 Hz, 1H), 5.01 (s, 1H), 3.48 (m, 4H), 2.95 (m, 4H), 2.31 (s, 3H).

(5) Synthesis of 2-tert-butoxycarbonylamino-3-[4-(2-methyl-10H-thieno[2,3-b][1,5]benzodiazepine-4-yl)-piperazin-1-yl]-propionic acid, methyl ester (E)

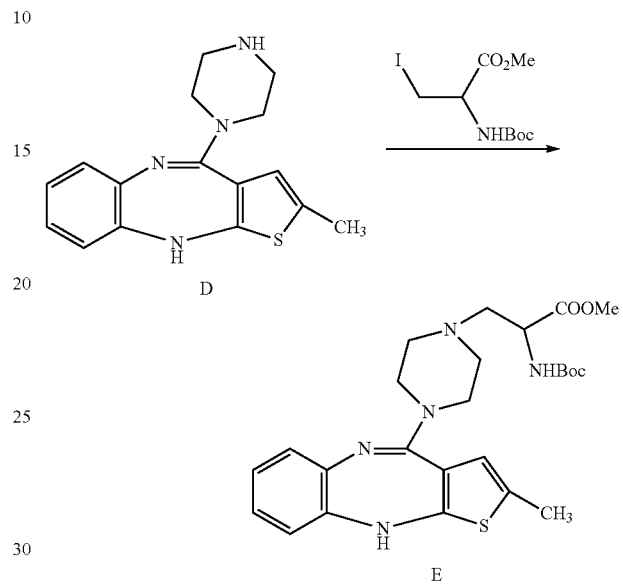

A mixture of D (200 mg, 0.67 mmol), Boc-iodo-Ala-OMe (220 mg, 0.67 mmol) and Na$_2$CO$_3$ (71 mg, 0.67 mmol) in dry acetone (17 ml) was refluxed overnight under nitrogen. The solvent was evaporated, the residue diluted with dry methanol (2 ml, distilled from magnesium), and the reaction mixture was stirred under N$_2$ overnight at 45° C. Methanol was evaporated. Chromatography on silica gel afforded E by elution with 1:1 EtOAc:hexanes; yield 48%.

$^1$H NMR (400 MHz, CDCl$_3$): δ 7.03 (d, J=7.6 Hz, 1H), 6.95 (t, J=7.6 Hz, 1H), 6.87 (t, J=7.6 Hz, 1H), 6.61 (d, J=7.5 Hz, 1H), 6.26 (s, 1H), 5.32 (br s, 1H), 4.35 (br m, 1H), 3.74 (s, 3H), 3.49 (br s, 4H), 2.73 (br m, 2H), 2.53 (br m, 4H), 2.30 (s, 3H), 1.45 (s, 9H). $^{13}$C NMR (100 MHz, CDCl$_3$): δ 172.6, 157.7, 155.5, 152.4, 142.9, 140.1, 129.1, 128.0, 124.6, 124.0, 122.8, 119.1, 80.0, 58.8, 53.2, 52.3, 51.9, 47.0, 28.3, 15.4.

(6) Synthesis of 2-amino-3-[4-(2-methyl-10H-thieno[2,3-b][1,5]benzodiazepin-4-yl)-piperazin-1-yl]-propionic acid, methyl ester hydrochloride salt (Compound 1-salt)

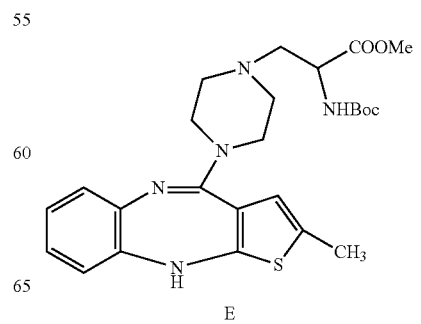

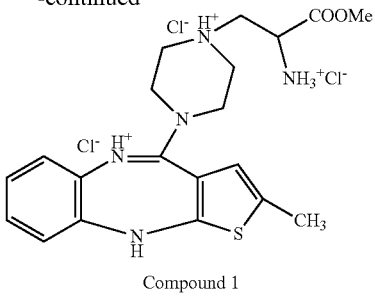

Compound 1

A mixture of E (80 mg, 0.16 mmol) and HCl/methanol (1.25 M, 2 ml) was stirred overnight. After evaporating the solvent, the residue was diluted with water and washed with ether. The aqueous solution was evaporated to dryness to give the protonated Compound 1; yield 92%.

$^1$H NMR (400 MHz, D$_2$O): δ 6.99 (dt, J=7.4 Hz, J=1.3 Hz, 1H), 6.83-6.92 (m, 2H), 6.63 (d, J=7.9 Hz, 1H), 6.16 (s, 1H), 4.50 (m, 1H), 3.78 (br s, 4H), 3.66 (s, 3H), 3.58 (dd, J=14.3 Hz, J=6.2 Hz, 1H), 3.34 (dd, J=14.3 Hz, J=6.3 Hz, 1H), 3.28 (br s, 4H), 2.02 (s, 3H). $^{13}$C NMR (100 MHz, D$_2$O): δ 167.4, 164.2, 160.5, 147.1, 132.3, 129.3, 127.2, 125.7, 125.1, 121.9, 120.1, 109.7, 55.1, 54.4, 52.1, 48.3, 47.5, 14.3. MS (FAB): calcd. for C$_{20}$H$_{26}$N$_5$O$_2$S (MH$^+$) 400.1, found 400.1.

Synthesis of Compound 2

(1) Synthesis of N-Boc-L-serine, ethyl ester (F)

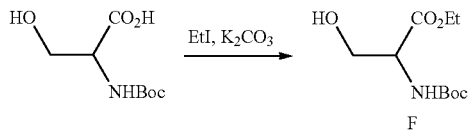

To a solution of Boc-Ser-OH (0.3 g, 1.46 mmol, 1 eq) in dry DMF (4 ml) at 0° C., dry K$_2$CO$_3$ (0.22 g, 1.6 mmol, 1.1 eq) was added. The resulting white suspension was stirred for 15 minute and ethyl iodide (0.68 g, 0.35 ml, 4.38 mmol, 3 eq) was dropwise added. The cooling was removed and reaction mixture was stirred at room temperature under N$_2$ for 24 h. To the formed white emulsion H$_2$O was added, and the mixture extracted by EtOAc. The combined organic layer was washed by H$_2$O and then brine, and dried over MgSO$_4$. The solvent was evaporated and the obtained oil was dried overnight in high vacuum. Yield of the pure F—0.27 g (79%).

$^1$H NMR (400 MHz, CDCl$_3$): δ 5.55(d, 1H), 4.27(m, 1H), 4.16(q, J=8.0 Hz, J=6.2 Hz, 2H), 3.79-3.90(m, 2H), 3.24(br s, 1H), 1.39 (s, 9H) 1.25(t, J=14.2 Hz, 3H).

(2) Synthesis of N-Boc-dehydroalanine, ethyl ester (G)

To a solution of Boc-L-serine ethyl ester, F, as prepared above, (0.45 g, 1.9 mmol, 1 eq) in dry DCM (10 ml) under N$_2$, triethylamine (0.3 ml, 2.1 mmol, 1.1 eq) was added and then dichloro-acetylchloride (0.2 ml, 2.1 mmol, 1.1 eq) was added dropwise. The reaction mixture was stirred at room temperature for 1 h and then the solution of DBU (0.31 ml, 2.1 mmol, 1.1 eq) in 2.5 ml of dry DCM was added. The dark blue solution was refluxed overnight under N$_2$. The cooled reaction mixture was poured to 5% citric acid solution in H$_2$O, extracted by DCM and the combined organic layer was washed by brine, dried over MgSO$_4$ and evaporated. The black oil residue was dried in high vacuum and yielded 0.5 g of intermediate dicholroacetyl derivative. This product was dissolved in 3 ml of dry DCM, then DBU (0.33 ml) in 2 ml DCM was added and reaction mixture was refluxed under N$_2$ overnight. The cooled solution was poured to 5% aqueous citric acid solution and extracted by DCM. The organic layer was washed with brine, dried over MgSO$_4$ and evaporated. The resulting black oil was purified by flash chromatography on silica gel (eluent—3% EtOAc in Hexanes).

Yield of the colorless oil product—0.23 g (58%)

$^1$H NMR (200 MHz, CDCl$_3$): δ 7.0(s, 1H), 6.1(s, 1H) 5.69(s, 1H), 4.24(q, J=14.2 Hz, 2H) 1.45(s, 9H), 1.29(t, J=7.1 Hz, 2H).

(3) Synthesis of 2-(N-Boc)amino-3-[4-(2-methyl-10H-thieno[2,3-b][1,5]benzodiazepin-4-yl)-piperazin-1-yl]-propionic acid, ethyl ester (H)

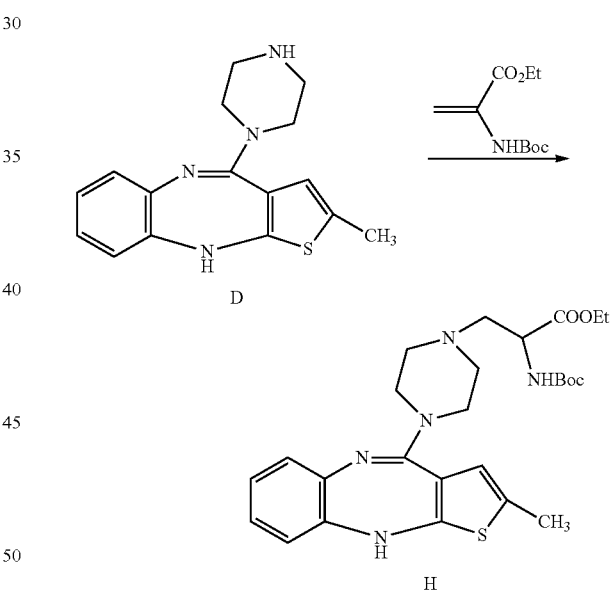

A mixture of 2-methyl-4-(1-piperazinyl)-10H-thieno[2,3-b][1,5]benzodiazepine, compound D above, (0.14 g, 0.46 mmol, 1 eq) and N-Boc-dehydroalanine ethyl ester (G, 0.1 g, 0.46 mmol, 1 eq) in 4 ml of anhydrous EtOH was refluxed at 60-65° C. overnight. The solvent was evaporated to dryness and the crude product was purified by flash chromatography (eluent—40% EtOAc in Hexanes). Yield—0.15 g (65%)

$^1$H NMR (400 MHz, CDCl$_3$): δ 6.95-7.01(m, 2H); 6.86(m, 1H); 6.60(d, J=7.9 Hz, 1H); 6.26(s, 1H); 5.35(br s, 1H); 4.33(br s, 1H); 4.16-4.20(m, 2H); 3.46(br s, 4H); 2.73(br s, 2H); 2.53-2.58(m, 4H); 2.22(s, 3H); 1.45(s, 9H); 1.29(t, J=7.1 Hz, 3H). $^{13}$C NMR (100 MHz, CDCl$_3$): δ 172.9, 158.4, 156.2, 152.6, 143.3, 141.6, 129.9, 128.9, 125.4, 124.6, 123.7, 120.2, 119.7, 80.7, 62.1, 59.7, 54.1, 52.8, 47.6, 29.1, 16.2, 14.9.

(4) Synthesis of 2-Amino-3-[4-(2-methyl-10H-thieno[2,3-b][1,5]-benzo diazepine-4-yl)piperazin-1-yl]propionic acid, ethyl ester trihydrochloride salt (Compound 2)

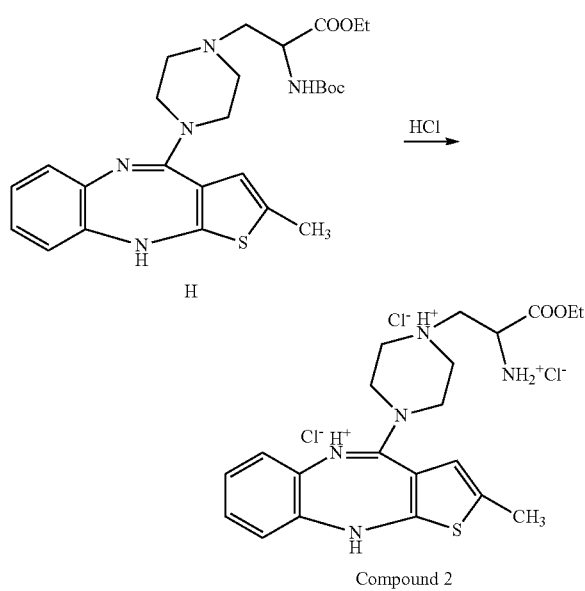

A mixture of 2-(N-Boc)amino-3-[4-(2-methyl-10H-thieno[2,3-b][1,5]benzodiazepin-4-yl)-piperazin-1-yl]-propionic acid, ethyl ester, H, (50 mg, 0.096 mmole) and HCl/ethanol (1.25 M, 2 ml) was stirred overnight at room temperature. The solvent was evaporated, the residue was diluted with water and washed with diethylether. The aqueous solution was lyophilized. Yield of Compound 2—30 mg (60%).

$^1$H NMR (400 MHz, CDCl$_3$): δ 7.20-7.15(m, 1H); 7.03-7.13(m, 2H); 6.85(d, J=8.0 Hz, 1H); 6.37(s, 1H); 4.37(m, 1H); 4.23(q, J=8.0 Hz, 2H); 3.78(br s, 4H); 3.26(dd, J=12.0 Hz, J=8.0 Hz, 1H); 3.10(m, 2H); 2.97(br s, 4H); 2.19(s, 3H); 1.20(t, J=8.0 Hz, 3H). $^{13}$C NMR (100 MHz, CDCl$_3$): δ 168.8, 163.8, 160.7, 147.8, 132.9, 129.9, 128.2, 126.3, 125.9, 122.9, 120.8, 111.2, 64.9, 56.2, 52.7, 50.6, 15.0, 13.8. MS (Fab): calcd. for C$_{21}$H$_{28}$N$_5$O$_2$S (MH$^+$) 414.4, found 414.2.

Synthesis of Compound 6

(1) Synthesis of N-Boc-N-methyl-L-serine, methyl ester (I)

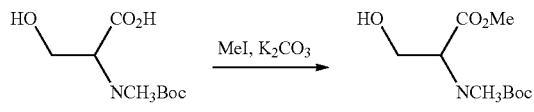

To a solution of Boc-N-Me-L-serine (0.5 g, 2.2 mmol, 1 eq) in dry DMF (2 ml) at 0° C. dry K$_2$CO$_3$ (0.35 g, 2.5 mmol, 1.2 eq) was added. The resulting white suspension was stirred for 15 minutes and methyl iodide (0.93 g, 0.42 ml, 6.6 mmol, 3 eq) was dropwise added. The cooling was removed and reaction mixture was stirred at room temperature under N$_2$ for 24 h; the progress of the reaction was monitored by TLC (EtOAc/Hexanes 4:6). To the formed white emulsion H$_2$O was added, and the mixture extracted by EtOAc (three times× 30 ml). The combined organic layer was washed by H$_2$O and then brine, dried over MgSO$_4$. The solvent was evaporated and the obtained colorless oil was dried overnight in high vacuum. Yield of the pure product I—0.4 g (76%).

Two aptamers are visible in NMR. $^1$H NMR (400 MHz, CDCl$_3$); δ 4.47(m, 1H), 4.03(m, 2H), 3.75-3.83(m, 2H), 3.13 (m, 1H), 3.69(s, 3H), 2.89(s, 3H), 2.85(s, 3H), 1.41(s, 9H), 1.37(s, 9H). $^{13}$C NMR (100 MHz, CDCl$_3$): δ 170.0, 170.6, 156.2, 154.9, 80.4, 80.2, 62.1, 61.1, 60.7, 60.6, 33.7, 33.1, 28.0.

(2) Synthesis of N-Boc-N-methyl dehydroalanine, methyl ester (J)

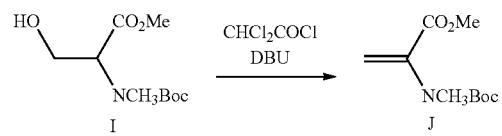

To a solution of Boc-N-methyl-L-serine methyl ester, I, (0.46 g, 1.9 mmol. 1 eq) in 10 ml dry DCM under N$_2$, triethylamine (0.29 ml, 2.2 mmol, 1.15 eq) was added and then dichloroacetylchloride (0.23 ml, 2.2 mmol, 1.15 eq) was added dropwise. The reaction mixture was stirred at room temperature for 1 h, then the solution of DBU (0.33 ml, 2.2 mmol, 1.15 eq) in 2.5 ml dry DCM was added, and the combined mixture was refluxed overnight.

The cooled reaction mixture was poured to 5% citric acid solution in H$_2$O, extracted by DCM, and the separated organic layer was washed by brine, dried by MgSO$_4$ and evaporated. The black oil residue (0.52 g) of the intermediate dichloroacetyl derivative was dissolved in 3 ml dry DCM and DBU (0.33 ml) in 2 ml DCM was added. The reaction mixture was refluxed under N$_2$ overnight. The cooled solution was poured to 5% citric acid aqueous solution, extracted by DCM, and the organic layer was washed by brine, dried by MgSO$_4$ and evaporated. The crude product was purified by flash chromatography on silica gel (elution with isocratic 10% EtOAc/Hexanes) to give the pure J—yield 0.2 g (48%). Drying of the product in high vacuum should be avoided.

$^1$H NMR (200 MHz, CDCl$_3$): δ 5.77(s, 1H), 5.30 (s, 1H), 3.75(s, 3H), 3.09(s, 3H), 1.39(s, 9H). $^{13}$C NMR (50 MHz, CDCl$_3$): δ 153.7, 141.3, 115.1, 80.9, 52.0, 36.4, 27.9.

(3) Synthesis of 2-(N-Boc-N-methyl)amino-3[4-(2-methyl-10H-thieno[2,3-b][1,5]benzodiazepin-4-yl)piperazin-1-yl]propionic acid, methyl ester (K)

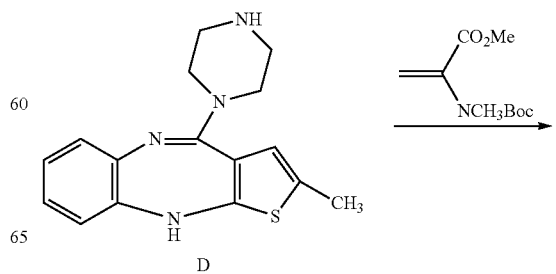

-continued

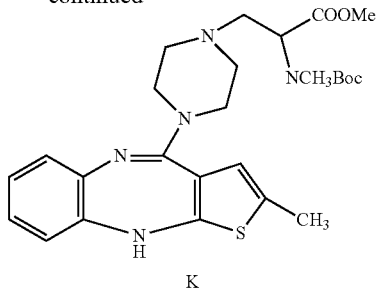

K

A mixture of 2-methyl-4-(1-piperazinyl)-10H-thieno[2,3-b][1,5]benzodiazepine, compound D above, (0.28 g, 0.93 mmol, 1 eq) and Boc-N-methyl dehydroalanine methyl ester, J, (0.2 g, 0.93 mmol, 1 eq) in 5 ml anhydrous MeOH was heated at 50° C. under $N_2$ overnight. The cooled solution was evaporated to dryness and the residue was purified by flash chromatography on silica gel (eluting with isocratic 50% EtOAc/Hexanes). Yield of pure K—0.3 g (63%).

$^1$H NMR (400 MHz, CDCl$_3$): δ 7.03(d, J=7.6 Hz, 1H), 6.95(t, J=7.6 Hz, 1H), 6.87(t, J=7.6 Hz, 1H), 6.60(d, J=7.5 Hz, 1H), 6.29(s, 1H), 5.02(m, 1H) 4.98(s, 1H), 4.57 (m, 1H), 3.76(s, 3H), 3.47 (s, 4H), 2.91 (br m, 2H), 2.84 (s, 3H), 2.68-2.90 (br m, 4H), 2.31(s, 3H) 1.47 (s, 9H). $^{13}$C NMR (100 MHz, CDCl$_3$): δ 172.15, 157.99, 155.6, 152.1, 142.9, 141.3, 129.4, 128.5, 125.0, 124.1, 123.4, 113.9, 119.3, 80.8, 80.4, 58.0, 57.5, 56.5, 55.7, 53.6, 53.4, 52.5, 47.3, 28.8, 15.8.

(4) Synthesis of 2-N-methylamino-3-[4-(2-methyl-10H-thieno[2,3-b][1.5]benzodiazepin-4-yl)-piperazin-1-yl]propionic acid, methyl ester trihydrochloride salt (Compound 6)

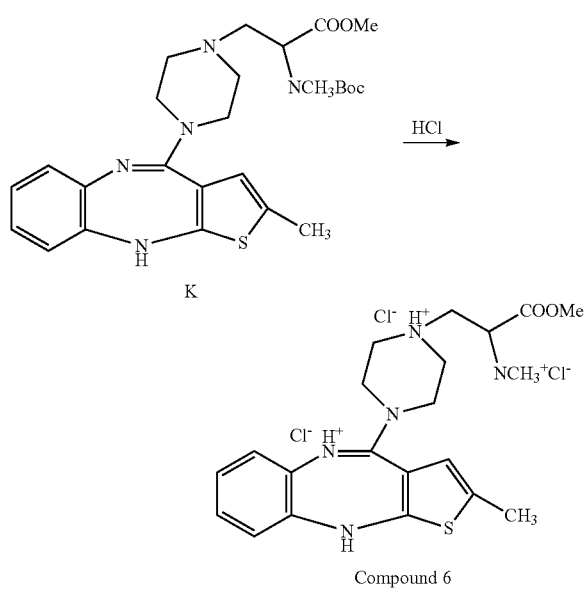

Compound 6

A solution of 2-(N-Boc-N-methyl)amino-3[4-(2-methyl-10H-thieno[2,3-b][1,5]benzodiazepin-4-yl)piperazin-1-yl] propionic acid, methyl ester, K, (0.3 g, 0.58 mmol) in HCL/ethanol (1.25 M, 8 ml) was stirred at room temperature overnight. The light yellow precipitate was formed and the suspension was decanted. The precipitate was washed several times with dry diethyl ether, and dried under vacuum.

Yield of Compound 6—0.26 g (87%).

$^1$H NMR (400 MHz, D$_2$O): δ 7.15(dq, J=6.6 Hz, J=2.3 Hz, 1H), 7.03-7.05(m, 2H), 6.82(d, J=7.8 Hz, 1H), 6.32(s, 1H), 4.26(m, 1H), 3.72(br s, 4H), 3.73(s, 3H), 3.30(dd, J=14.3 Hz, J=5.7 Hz, 1H), 2.97(br s, 4H), 2.74(s, 3H), 2.17(s, 3H). $^{13}$C NMR (100 MHz, D$_2$O): δ 167.6, 163.0, 159.7, 146.9, 131.9, 128.9, 127.16, 125.4, 124.9, 122.0, 119.8, 110.1, 57.0, 54.2, 53.9, 51.7, 48.6, 31.7, 14.1. MS (FAB): calcd. for $C_{21}H_{27}N_5O_2S$ (MH$^+$) 413.5, found 414.3. EA (%): calcd. for $C_{21}H_{31}Cl_3N_5O_3S$ (M.3HCl.H$_2$O): C, 46.58; H, 5.91; Cl, 19.65; found: C, 45.94; H, 6.18; Cl, 19.52.

Synthesis of Compound 14

(1) Synthesis of O-Allyl-N-Boc-L-serine methyl ester (L)

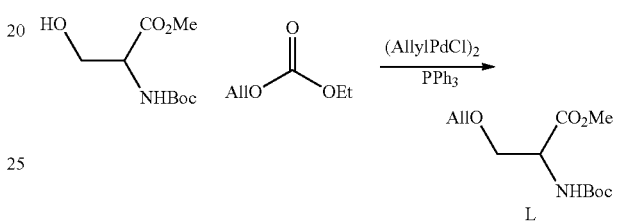

L

To a stirred solution of N-Boc-L-serine methyl ester (0.22 g, 1 mmol, 1 eq) in dry THF (2 ml) under $N_2$ a mixture of π-allylpalladium chloride dimer (0.01 g, 0.02 mmol), triphenylphosphine (0.024 g, 0.09 mmol) and allyl ethyl carbonate (0.26 ml, 2 mmol, 2 eq) in dry THF (1 ml) was dropwise added at room temperature.

The reaction mixture was refluxed under $N_2$ overnight. The solvent was evaporated and the crude product was purified by flash chromatography on silica gel (elution with isocratic 10% EtOAc/Hexanes) to give the pure compound. Yield of L was 0.14 g (63%).

$^1$H NMR (400 MHz, CDCl$_3$): δ 5.75-5.85 (m, 1H), 5.36 (m, 1H), 5.13-5.23 (m, 2H) 3.93-3.95 (m, 2H), 3.82 (dd, J=3.0 Hz, J=6.4 Hz, 1H), 3.72 (s, 3H), 3.61 (dd, J=3.3 Hz, J=9.4 Hz, 1H), 1.44 (s, 9H). $^{13}$C NMR (100 MHz, CDCl$_3$): δ 171.0, 155.3, 133.8, 117.2, 79.7, 72.0, 69.7, 53.8, 52.2, 28.1.

(2) Synthesis of O-(3-Iodopropyl)-N-Boc-L-serine methyl ester (M)

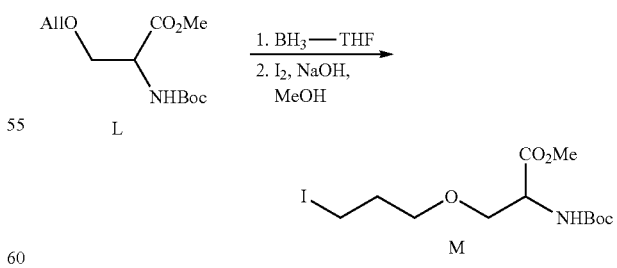

M

To a solution of O-Allyl-N-Boc-L-serine methyl ester, L prepared as above, (0.25 g, 1 mmol, 1 eq) in dry THF (1 ml) equimolar amount of 1M BH$_3$-THF complex solution in THF (0.96 ml) was dropwise added at 0° C. After addition, the colorless solution was heated at 55° C. under $N_2$ for 1.5 h. The progress of the reaction was monitored by TLC (20% EtOAc/

Hexanes). To a cooled reaction mixture (0° C.) I₂ (0.17 g, 0.67 mmol) was added, followed by solution of NaOH in MeOH (0.24 ml, 3M). The formed dark solution was stirred under N₂ at room temperature for 2 h.

The reaction mixture was then poured into a 1 M solution of sodium thiosulfate in H₂O and extracted by EtOAc (three times with 20 ml). The combined organic layer was washed by brine and dried over MgSO₄. The solvent was evaporated and the crude was purified by flash chromatography on silica gel (elution with isocratic 20% EtOAc/Hexanes) to give the pure M in 25% yield (0.093 g).

¹H NMR (400 MHz, CDCl₃): δ 5.32 (d, J=8.0 Hz, 1H), 4.4 (m, 1H), 3.81 (dd, J=3.2 Hz, J=9.4 Hz, 1H), 3.66 (s, 3H), 3.64 (dd, J=3.2 Hz, J=9.4 Hz, 1H), 3.44-3.51 (m, 2H), 3.19 (t, J=6.6 Hz, 2H), 1.98 (quint, J=6.1 Hz, 2H), 1.44 (s, 9H). ¹³C NMR (100 MHz, CDCl₃): δ 171.8, 156.2, 80.7, 71.6, 71.3, 70.7, 54.7, 53.3, 33.7, 29.0, 3.2.

(3) Synthesis of 2-(N-Boc-amino)-3-[O-propyl-3-(4-(2-methyl-10H-thieno[2,3-b][1,5]benzodiazepine-4-yl)piperazin-1-yl]propionic acid, methyl ester (N)

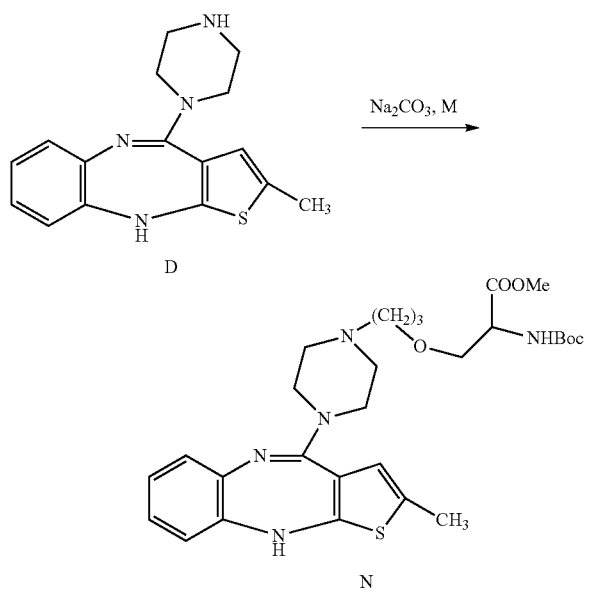

A mixture of 2-methyl-4-(1-piperazinyl)-10H-thieno[2,3-b][1,5]benzodiazepine, (compound D, 0.073 g, 0.24 mmol, 1 eq), O-(3-Iodopropyl)-N-Boc-L-serine methyl ester (M, 0.093 g, 0.24 mmol, 1 eq) and dry Na₂CO₃ (0.025 g 0.24 mmol, 1 eq) in 8 ml anhydrous acetone was refluxed under N₂ overnight. The cooled reaction mixture was evaporated to dryness; 20 ml CHCl₃ was added to the residue and the precipitate of NaI was filtered off. The solvent was evaporated and the crude product was purified by flash chromatography on silica gel (eluting with gradient: 3% MeOH in CHCl₃ to 5% MeOH in CHCl₃) to give the pure N. Yield 0.1 g (77%).

¹H NMR (400 MHz, CDCl₃): δ 7.04 (d, J=7.6 Hz, 1H), 6.97 (t, J=7.6 Hz, 1H), 6.95 (t, J=7.6 Hz, 1H), 6.62 (d, J=7.6 Hz, 1H) 6.28 (d, J=0.9 Hz, 1H), 5.48 (d, J=8.4 Hz, 1H), 5.01 (s, 1H), 4.42 (m, 1H), 3.84 (dd, J=9.3 Hz, J=2.6 Hz, 1H), 3.75 (s, 3H), 3.63 (dd, J=9.5 Hz, J=3.2 Hz, 1H), 3.57 (m, 4H), 3.47 (m, 2H), 2.55 (m, 4H), 2.46 (m, 2H), 2.30 (s, 3H), 1.77 (quint, J=6.6 Hz, 2H), 1.45 (s, 9H). ¹³C NMR (100 MHz, CDCl₃): δ 172.1, 158.3, 156.3, 152.5, 143.2, 141.7, 129.8, 128.8, 125.4, 124.5, 123.7, 120.3, 119.7, 80.8, 71.5, 70.5, 55.9, 54.8, 53.9, 53.2, 47.5, 29.1, 27.5, 16.2.

(4) Synthesis of 2-Amino-3-[O-propyl-3-(4-(2-methyl-10H-thieno[2,3,-b][1,5]-benzodiazepine-4-yl)piperazin-1-yl]propionic acid, methyl ester, trihydrochloride salt (Compound 14)

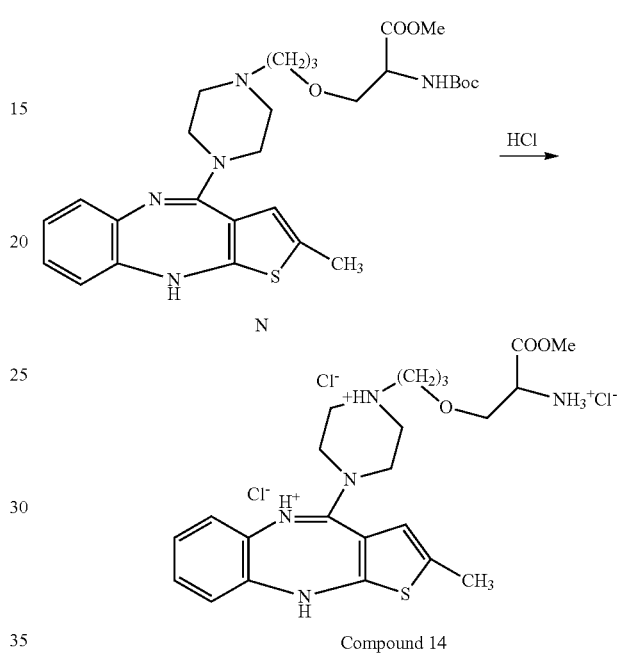

Compound 14

A mixture of 2-(N-Boc-amino)-3-[O-propyl-3-(4-(2-methyl-10H-thieno[2,3-b][1,5]benzodiazepine-4-yl)-piperazin-1-yl]propionic acid, methyl ester, N, (100 mg, 0.18 mmol) and HCl/MeOH (1.25M, 3 ml) was stirred overnight at room temperature. The solvent was evaporated; the residue was diluted with water and washed with diethyl ether. The aqueous solution was lyophilized. Yield of Compound 14: 78 mg (95%).

¹H NMR (400 MHz, D₂O): δ 7.19-7.23 (m, 1H), 7.05-7.11 (m, 2H), 6.87 (d, J=8.0 Hz, 1H), 6.41 (s, 1H), 4.30 (t, J=3.9 Hz, 1H), 3.93 (dd, J=4.3 Hz, J=11.0 Hz, 2H), 3.81 (dd, J=3.2 Hz, J=11.0 Hz, 2H), 3.76 (s, 3H), 3.75 (br s, 4H), 3.57 (m, 2H), 3.26 (m, 6H), 2.22 (s, 3H), 1.98 (m, 2H). ¹³C NMR (100 MHz, D₂O): δ 169.46, 165.2, 161.7, 148.0, 133.4, 130.2, 128.0, 126.4, 126.1, 122.5, 120.9, 110.8, 68.7, 68.2, 55.3, 54.5, 53.8, 51.7, 47.6, 24.3, 15.0. MS (FAB): calcd for C₂₃H₃₁N₅O₃S (MH⁺) 457.5, found 458.2.

B. Animal Behavioral Models

In the following tests, unless otherwise indicated, male ICR or Balb/C mice, 6 to 8 weeks of age were used. All animals were housed (4-5/cage) under controlled conditions (temperature, light, humidity) given food and water ad libitum and allowed for 5-7 days of acclimatization before the beginning of experimentation.

Compound of the invention such as Compounds 1, 3 or 6, or olanzapine were administered orally to the mice at an equimolar dose and the behavioral tests were performed 1-4 hr later. The following tests were performed:

(a) A forced swim test,
(b) An open field exploration, and
(c) An amphetamine-induced hyperactivity.

The forced swim test and the open field exploration tests were documented by a digital video camera linked to behavioral analysis software (Noldus Information Technology, Netherlands).

Forced Swim Test (FST)

This is one of the most widely used tools for screening antidepressant activity pre-clinically in acute treatment. The test was first described by Porsolt et al., (Behavioral despair in mice: a primary screening test for antidepressants. *Arch. Int. Pharmacodyn. Ther.* 229, pp. 327-336, 1977). The FST test is based on the observation that rats and mice develop an immobile posture when placed in an inescapable cylinder of water. This behavior is considered a behavioral despair as opposed to active form of coping with stressful conditions. The FST test is considered a good screening tool with good reliability and predictive validity.

Three parameters were defined in the evaluation of FST:

1. Immobility—defined in the traditional Porsolt test as when no additional activity is observed other than that required to keep the animal's head above water;

2. Swimming behavior—being the movement (usually horizontal) throughout the chamber that also includes crossing into another quadrant;

3. Climbing behavior—being defined as the upward-directed movements (vertical) of the forepaws along the side of the swim chamber.

The test in mice was conducted acutely (60-90 minutes post oral drug administration) and animals were dropped to the cylinder for 6 minutes and scoring was performed in the last 4 minutes after 2 minutes of adaptation.

Round glass cylinders, 18 cm in diameter and 20 cm deep were used. Water temperature was 24-28° C. Four parameters were taken: immobility, velocity, distance and strong mobility. The immobility in the animals was defined by activity lower than 10% movement of the center of gravity of the animal. Swimming was defined by the distance and the velocity of the animal, and climbing was related to strong mobility (movement of center of gravidance more than 30%).

Open Field Exploratory Locomotor Activity

The procedure consists of subjecting an animal, usually a rodent, to an unknown large environment from which escape is prevented by surrounding walls. The open field test is now one of the most popular procedures in animal psychology (Crawley, et al., Exploratory behavior models of anxiety in mice, *Neurosci Biobehav Rev* 9 (1985), pp. 37-44). The procedure involves forced confrontation of a rodent with the situation. The animal is placed in the center or close to the walls of the apparatus and the following behavioral items are recorded for a period ranging from 5 to 20 minutes: horizontal locomotion, and frequency of rearing or leaning. In such a situation, rodents spontaneously prefer the periphery of the apparatus to activity in the central parts of the open field. Increase in time spent in the central part as well as of the ratio central/total locomotion or decrease of the latency to enter the central part are indications of anxiolysis.

In a typical test, an individual mouse was placed in a novel environment of a square open field (50×50 cm), the floor of which had been divided into 3 areas, as shown below. The area within 10 cm of the chamber walls was termed the periphery. Animals were treated with a compound of the invention such as Compound 1, 3 or 6 with olanzapine or with a vehicle. One hour after drug administration, the animal was placed in the same corner of the field. The animal behavior in the open field was recorded by videotaping for 20-60 minutes and analyzed subsequently digitally using the Noldus software for animal behavior. The measurements included velocity, distance moved, frequency of visits to the central area, number of rearing events.

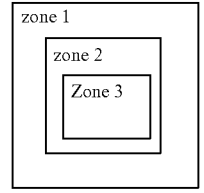

Amphetamine-induced Hyperactivity

The amphetamine-induced hyperactivity and motility is one of the most popular animal models for schizophrenia (Pouzet B, et al., Effects of the 5-HT(7) receptor antagonist SB-258741 in animal models for schizophrenia. *Pharmacol Biochem Behav* April; 71(4):655-665, 2002 and Geyer, et al., Animal behavior models of the mechanisms underlying antipsychotic atypicalicity, *Progress in Neuro-Psychopharmacol & Biological Psychiatry*, 27, 1071-79, 2003). Amphetamines are known to augment dopaminergic and noradrenergic neurotransmission by inducing catecholamine release and preventing catecholamine reuptake The experiment was conducted with ICR male mice placed in individual barrels. Olanzapine, or Compound 1 (for example at a dose of 10 and 20 mg/kg) were administered interperitoneal (i.p.) to the mice 0.5 hour prior to subcutaneous (s.c.) administration of amphetamine (3 mg/kg). The locomotor activity, number of rearings and head movements was recorded every 15 minutes for 2 h.

MK-801-Induced Stereotype Behavior in Rats (in Open Field)—

MK-801 is an analogue of PCP which inhibits NMDA receptors and elicits hyperlocomotion and stereotypic behavior in rodents and is used as an animal model of schizophrenia (Stephen, et al., Topiramate antagonizes MK-801 in an animal model of schizophrenia, *Eur. J. Pharmacol.* 449, 2002, 121-5). For experimentation, naïve Balb/c mice were used. MK-801 (0.15 mg/kg i.p) was administered 40 minutes after Compound 1 (or any one of the other compounds of the invention) or a vehicle, and 20 minutes prior to placing the mouse in an open field.

Animals placed in the open field were followed for 60 minutes and their distance moved, velocity, duration of immobility, and number of rearing events were registered using the Noldus system.

As stated above, MK-801 inhibits NMDA receptors and elicits hyperlocomotion. Therefore, where an antagonism of the hyperactivity-induced by the MK-801 is observed upon administration of a compound of the invention, it is an indication as to the positive modulation of the NMDA activity. In other words, such a compound may be considered as useful in the treatment of schizophrenia.

Catalepsy

Catalepsy in mice and rats serves as a behavioral model for the manifestation of the extrapyramidal adverse effects of neuroleptics (Worm, et al., Dopamine-like activities of an aminopyridazine derivative, CM 30366. A behavioral study, *Naunyn-Schmeideberg's Arch Pharmacol*, 334, 246-52, 1986).

Catalepsy in mice is evaluated using a bar test. The mice were placed in the middle of a steel rod situated between two platforms with their front paws resting on the bar. Animals were injected i.p. with a vehicle or Compound 1. Animals were scored 90 minutes later for the time it took each animal to reach the platform.

The Elevated Plus Maze

The elevated plus maze is a widely used method to test anxiety in rodents (Pellow, et al., *Pharmacol. Biochem. Behav.*, 24, 525-529 (1986)). The apparatus was made of wood and painted black, with two opposing open arms and two opposite enclosed arms of the same size. The arms were attached to a central square shaped in a plus sign. The whole apparatus was placed 50 cm above the floor. Anxious animals refrain from entering the open arm and prefer the closed arm. Benzodiazepines were shown to increase the time spent in the open arms and the frequency of entries to the open arms (Pellow, et al., Validation of open:closed arm entries in an elevated plus-maze as a measure of anxiety in the rat, *J. Neurosci. Methods*, 14, 149-167 (1985)).

In a typical experiment, Balb/c male mice were administered orally with 10 and 20 mg/kg of Compound 1 or Compound 6 and with a vehicle or with diazepam (1 mg/kg) administered per os (p.o.) 90 minutes before they were placed in the center of the maze. The frequency to the open aims, the time spent in the different arms, the velocity and number of rearings of the animals in each zone were recorded (Noldus). Mice treated with a compound of the invention and exhibit preference of entering to the open arms, or the center, and demonstrate a decrease in the time spent in the closed arms, are indicative of anxiolytic activity imposed by the compound.

The Morris Water Maze

The Morris Water Maze is a well known test aimed to assess spatial cognitive tasks (Anger, et al., Animal test systems to study behavioral dysfunctions of neurodegenerative disorders, *Neurotoxicology*, 12, 403-13 (1991)). The maze consists of a circular pool measuring 1.80 m in diameter 60 cm in height. The pool was filled with water (21±1° C.) to a depth of 30 cm. A circular hidden escape platform (10 cm in diameter) was placed just below the water surface. The test room contained several permanent extra maze cues such as the rat housing rack, laboratory table, posters on the walls, etc.

C. Results and Discussion

The effect of Compound 1 on the behavior of mice in the open field and the dose-dependent effect following i.p administration were evaluated. Naïve male Mice (Balb/c, Harlan Israel) were used. The animals, divided 3 to 5 animals per group, were administered with Compound 1 (12.5, 25, 50, 75 and 100 mg/kg) 1 hr prior to placing each in an open field. Mice were monitored for 1 hr (every 5 minutes) using the Noldus system, and their distance moved, velocity, time of immobility and number of rearings was recorded.

As FIGS. 1A-D indicate, Compound 1 induced a dose dependent decrease in the horizontal and vertical motility of the mice. At 12.5 mg/kg the drug did not modify significantly neither parameter and tended to increase rearing frequency. Moreover, doses up to 50 mg/kg induced a mild inhibition of the horizontal and the vertical motility. Higher doses showed a marked sedative effect and motility was reduced to minimum.

The effect of Compound 6 on the behavior of mice in the open field was also examined. Naïve male mice (Balb/c, Harlan Israel) were used. Animals (6 per group) were administered with Compound 6 (12.5, 25 and 50 mg/kg, i.p.) 1 hr prior to placing each in the open field. Mice were followed for 1 hr (every 5 minutes) using the Noldus system, and their distance moved, velocity, time of immobility and number of rearings was recorded.

As FIGS. 2A-D show, Compound 6 induced a dose dependent decrease in the motility of the mice expressed by decreased distance moved and velocity. The effect was mild up to 50 mg/kg. Compound 6 induced inhibition of the horizontal (distance) and the vertical motility (number of rearings). The drug increased the duration of "not moving" periods at all doses. It can thus be concluded that Compound 6 as is the case with Compound 1 has a mild sedative effect, as reflected by decreasing horizontal and vertical activity, mainly due to increased periods of immobility.

The effect of Compound 6 on the distance moved in Balb/c mice exposed to MK-801 (15 mg/kg) i.p. and to Compound 6 (up to 12.5 mg/kg, i.p.) administered 1 hr prior to MK-801 was also tested. The results indicate that Compound 6 did not cause a consistent dose dependent effect on the motility of the MK-801 treated mice. The data suggests that Compound 6 is a mild agent for the treatment of glutamate NMDA hypoactivity.

The effect of oral administration of Compound 1 in the open field was tested by orally administering to male ICR mice varying amounts of Compound 1 (5, 10 and 20 mg/kg) or vehicle. Animals were placed in the open field 1 hr after drug administration and horizontal and vertical behavior was recorded for 20 minutes.

Figure 3A:
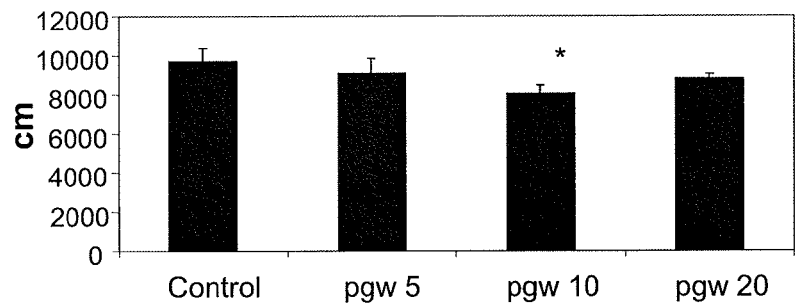
FIGS. 3A-C show the effect of oral administration of Compound 1 on the horizontal and vertical behavior of mice.
Figure 3B:
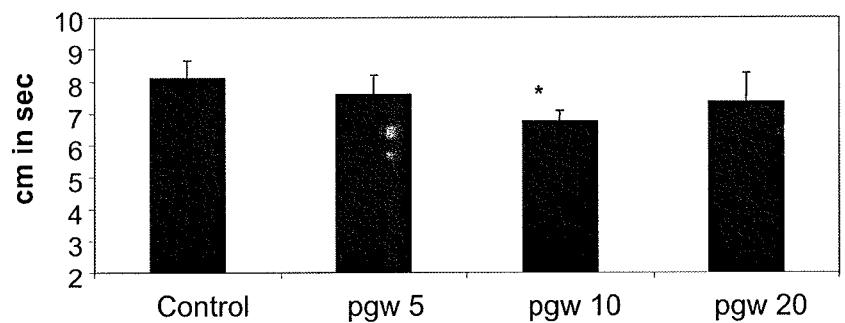
Figure 3C:
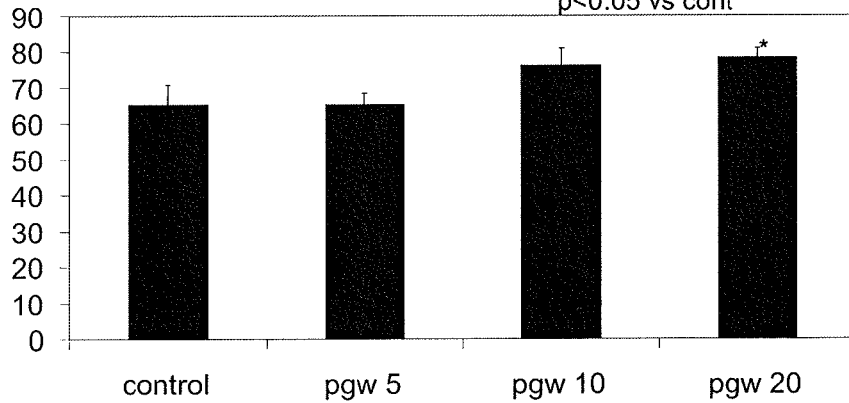

As FIGS. 3A-C show, oral administration of Compound 1 at 10 and 20 mg/kg slightly decreased the horizontal behavior as evidenced by the decrease in velocity and distance moved, and increased the vertical behavior as evidenced by increase in the number of rearings. It seems that the decreased velocity and distance moved are related to more time that the animal spent in the vertical position. The data also suggests that Compound 1 induces a slight increase in vigilance and/or stimulation; this effect may also be relevant to a stimulatory effect on cognition and learning.

The dose-dependent effect of Compound 3 administered i.p. in the open field was also tested. Naïve male mice (Balb/c, Harlan Israel) were used. Animals were administered with Compound 3 (12.5, 25 and 50 mg/kg, i.p., 6 per group) 1 hr prior to placing each in the open field. Mice were followed for 1 hr (every 5 minutes) using the Noldus system, and their distance moved, velocity, time of immobility and number of rearings was recorded.

Figure 4A:
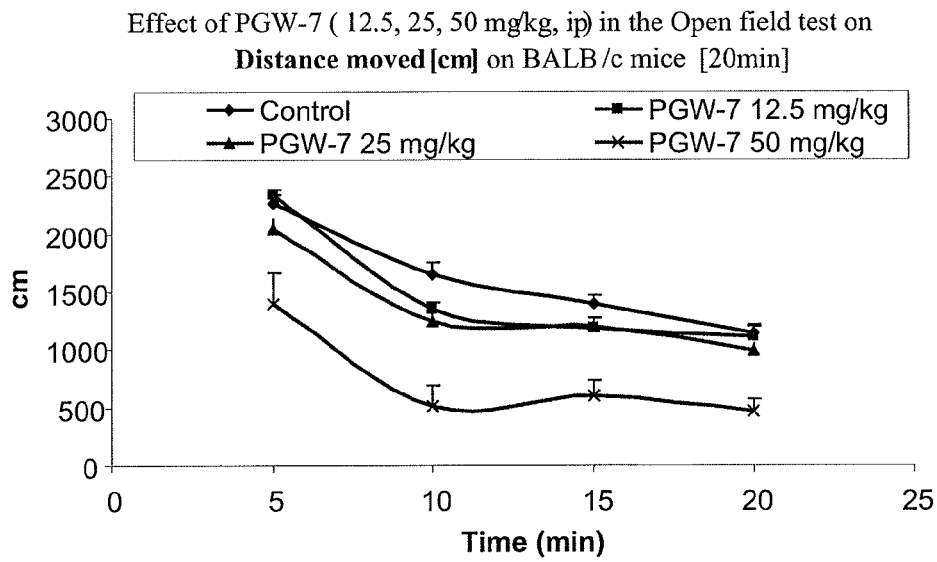
FIGS. 4A-C show the effect of Compound 3 (PGW-7) (12.5, 25 and 50 mg/kg, each point is the mean+/−SEM of 6 determinations) in the open filed test.
Figure 4B:
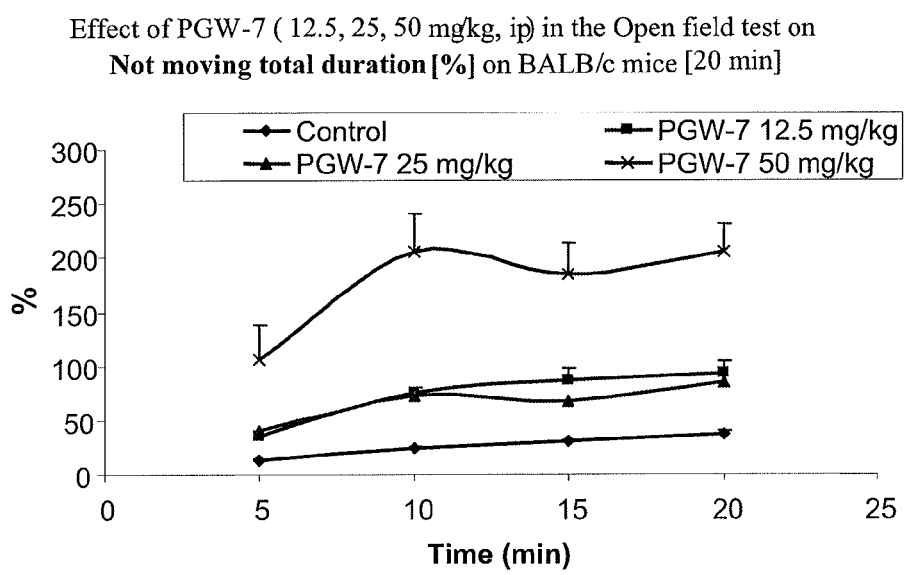
Figure 4C:
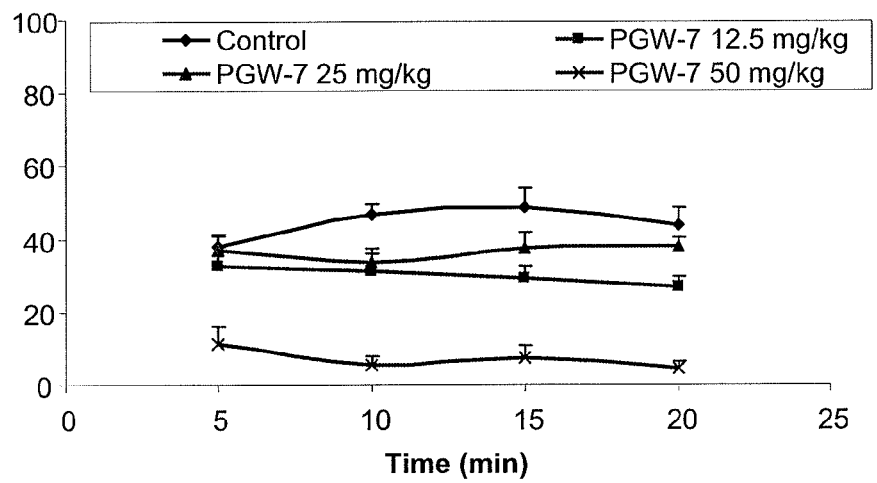

FIGS. 4A-C show the behavioral parameters of Compound 3 in the open field. Compound 3 induced a mild decrease in the motility of the mice expressed by decreased distance moved and velocity up to 25 mg/kg and a marked decrease in the motility parameters at 50 mg/kg (FIG. 4A). The drug dose dependently increased the duration of "not moving" periods (FIG. 4B) and decreased the number of rearings vs. controls (FIG. 4C).

Comparison between Compound 1, Olanzapine or D-serine on Anxiety Parameters in Mice in the Open Field Paradigm The effect of Compound 1, olanzapine and D-Serine [20 mg/kg, orally), administered 1 hr before placing the male ICR mice in the open field on anxiety parameters was examined in an open filed of the construction shown above. Animals were administered orally with Compound 1 (5, 10 and 20 mg/kg) or with a vehicle. Animals were placed in the open field 1 hr after drug administration and animal track was registered for 20 minutes. The time spent in the center (zone 3) and the frequency to the center were indicators of anxiety. High frequency and duration in the center indicated anxiolytic activity.

Figure 5:
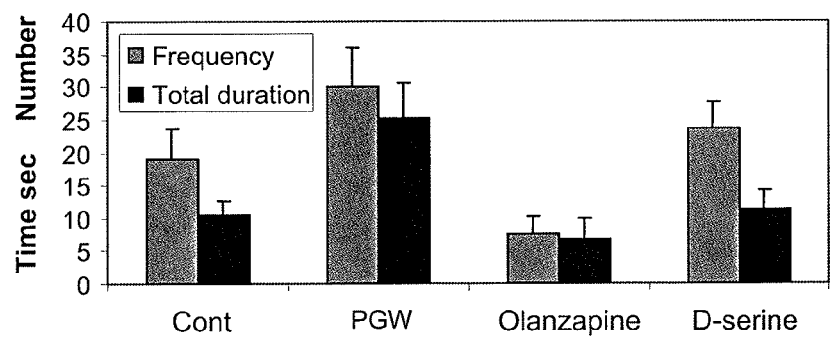
FIG. 5 shows the effect of Compound 1, olanzapine and D-serine (20 mg/kg, p.o) on time spent in the center of an open filed and on frequency to the center.

The results shown in FIG. 5 suggest that Compound 1 possesses anxiolytic activity which differs from olanzapine or D-serine.

Amphetamine-induced Hyperactivity and Stereotypic Behavior in Mice

As stated above, the amphetamine-induced hyperactivity and motility is one of the most popular animal models for schizophrenia. The experiment was conducted with ICR male mice placed in individual barrels. Compound 1 (20 mg/kg) was administered p.o to the mice 1 hr prior to i.p. administration of amphetamine (2. mg/kg). The hyper-active behavior expressed by the number of climbings and rearings and the stereotypic behavior expressed by the number of head movements was recorded every 15 minutes over a period of 1 h.

Figure 6A:
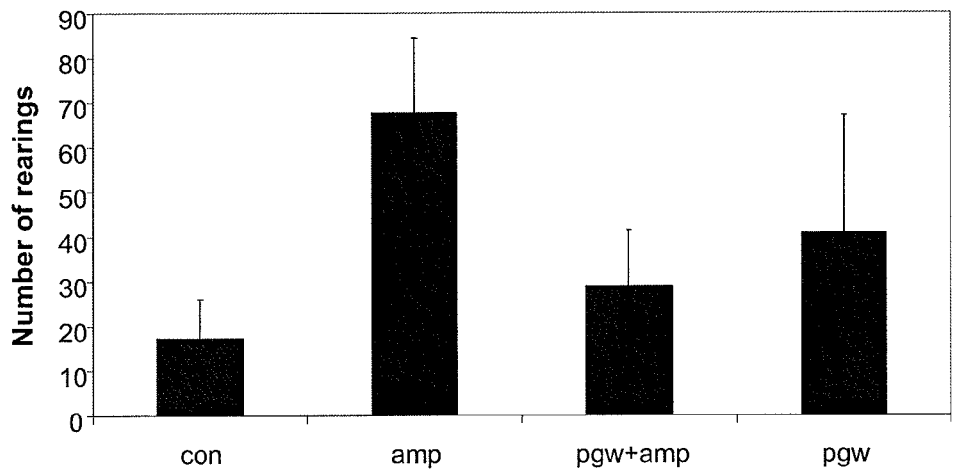
FIGS. 6A-B show the effect of Compound 1 (20 mg/kg, p.o.) on amphetamine-induced hyperactivity as manifested by the total number of rearings and climbings over a period of 1 hr (FIG. 6A) and the effect of Compound 1 (20 mg/kg, p.o.) on number of head movements (FIG. 6B).
Figure 6B:
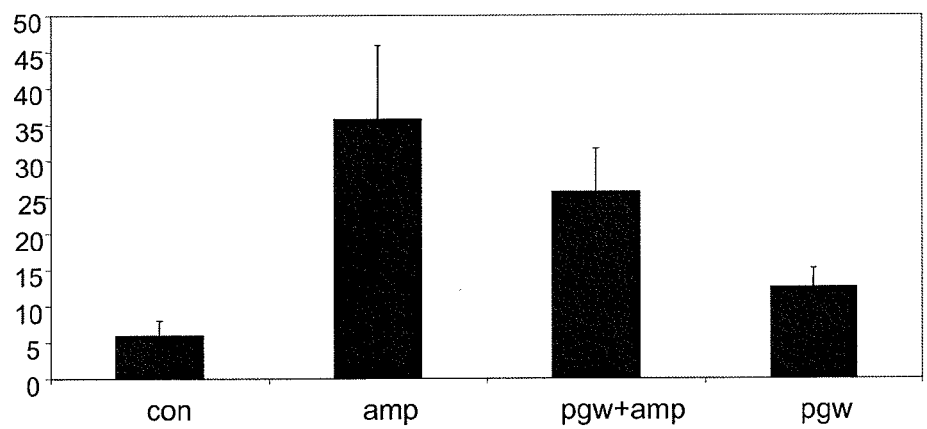

As FIGS. 6A-B show, Compound 1 was effective in antagonizing hyperactivity-induced by amphetamine. On the other hand, Compound 1 alone increased the rearing behavior as compared to control animals. Similar results were obtained also in the open field experiment. Moreover, Compound 1 did not attenuate the increase in head movements-induced by amphetamine. Overall, the data suggests a partial antagonist effect of Compound 1 at low doses against amphetamine-induced hyperactivity. High efficacy was found in antagonizing increased motility, without affecting the stereotypic behavior. These data point for an efficacy of Compound 1 against psychotic symptoms, without inducing extrapyramidal symptoms.

The effect of Compound 3 (12.5, 25 and 50 mg/kg, i.p.) on amphetamine-induced hyperactivity in Balb/c mice was also examined. Animals (6 per group) were injected with Compound 3 (12.5, 25 and 50 mg/kg) and 30 minutes later received amphetamine (2 mg/kg ip). After 30 minutes, animals were exposed to an open field test for a period of 20 minutes. Results show that Compound 3 dose-dependently antagonized the effect of amphetamine and decreased hypermotility. Compound 3 combined with amphetamine dose-dependently increased immobility and was effective already at 12.5 mg/kg, i.p. This indicates that Compound 3 is highly effective against hyper-domaminergic activity as manifested by amphetamine treatment.

Figure 7A:
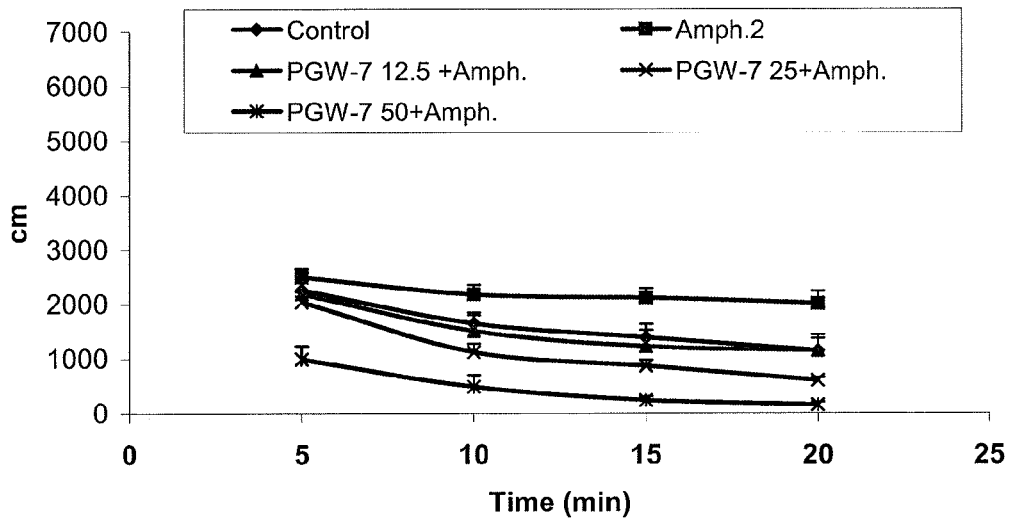
FIGS. 7A-B show the effect of Compound 3 (PGW-7) (12.5, 25, 50 mg/kg, i.p.), amphetamine (2 mg/kg, i.p.) and a combination thereof in the Open field test on distance moved (FIG. 7A) and immobility total duration (FIG. 7B).
Figure 7B:
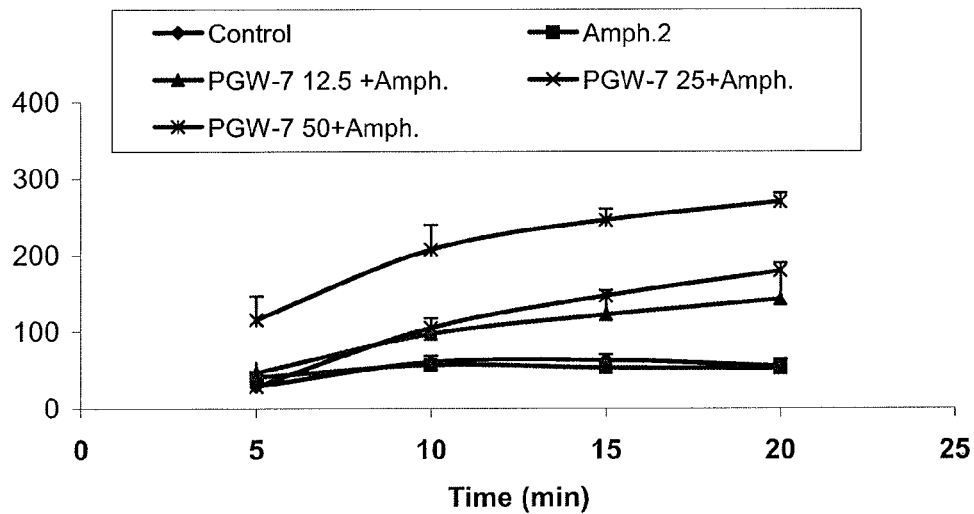
Figure 8A:
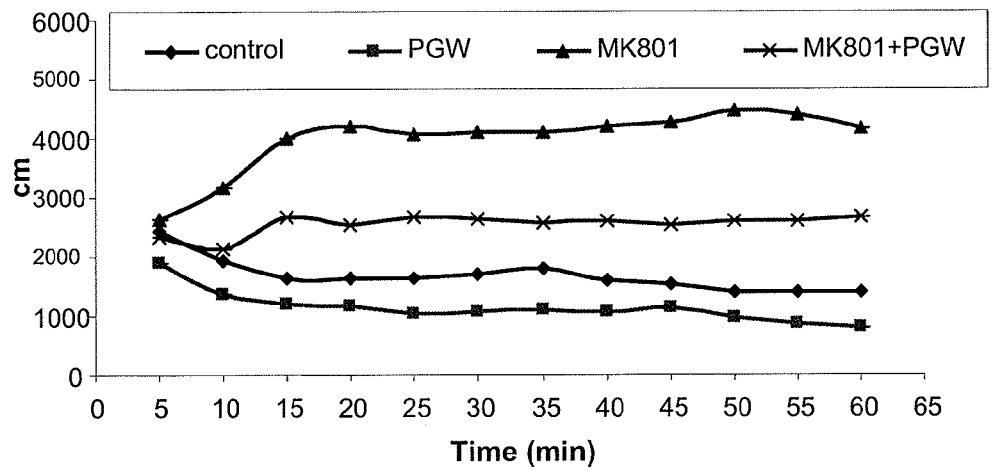
FIGS. 8A-E show the effect of Compound 1 (PGW), MK-801 and a combination thereof in the open field test on the distance moved (FIG. 8A); velocity mean (FIG. 8B); strong mobility total duration(s) (FIG. 8C); "not moving" total duration (FIG. 8D); and rearing frequency (FIG. 8E).
Figure 8B:
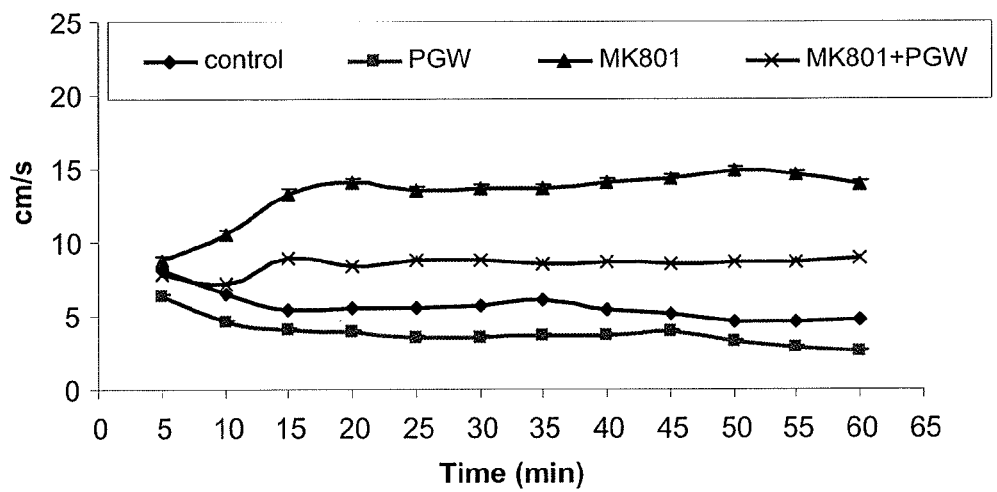
Figure 8C:
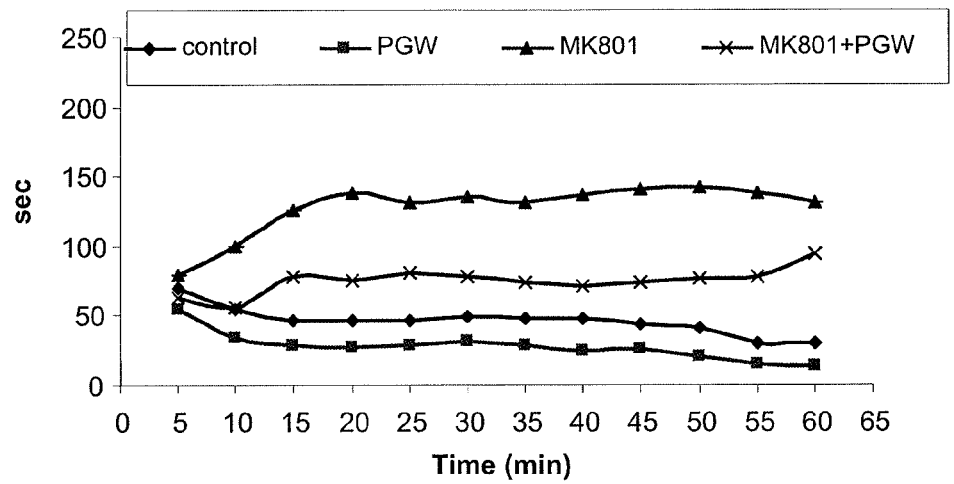
Figure 8D:
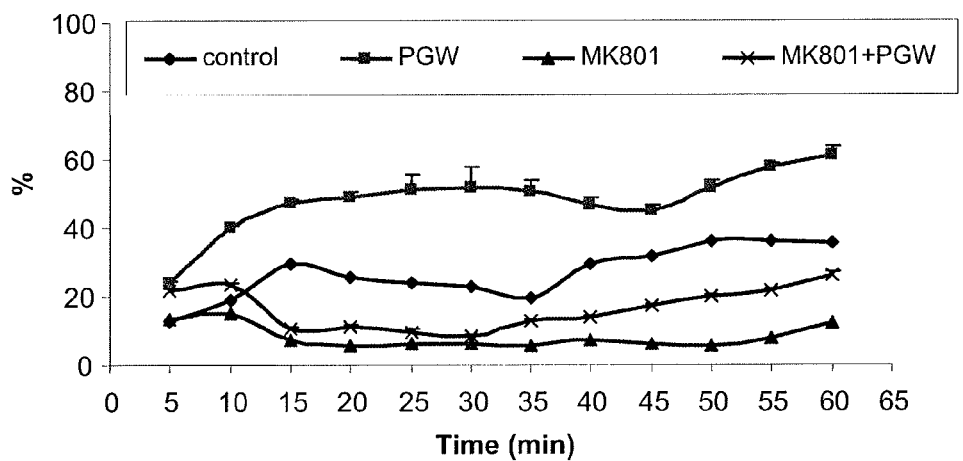
Figure 8E:
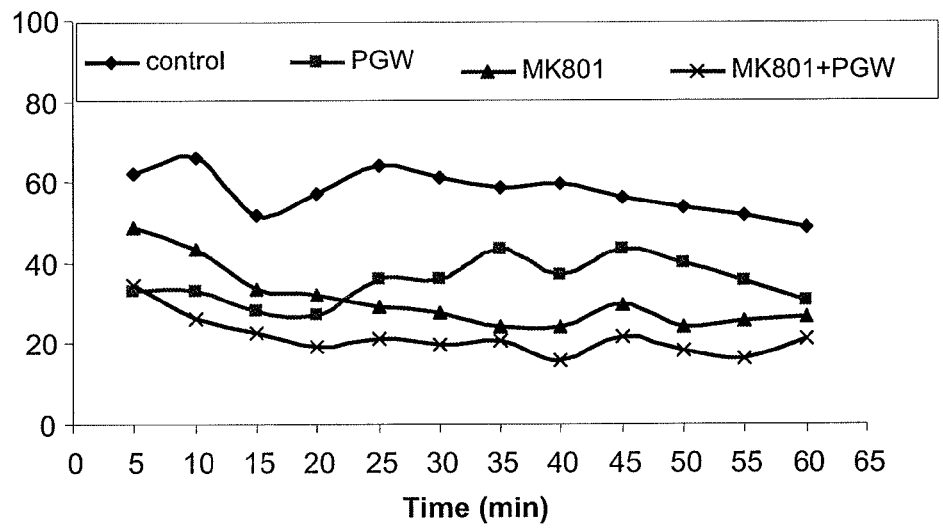

FIG. 7A shows the effect of Compound 3 (12.5, 25 and 50 mg/kg. i.p at −60 minutes) on distance moved. Results demonstrate a dose-dependent decrease in the distance moved with normalization at 12.5 mg/kg and a marked decrease at higher doses. FIG. 7B shows the immobility time of amphetamine and amphetamine combined with Compound 3. The results show that amphetamine was similar to controls yet Compound 3 already at 12.5 mg/kg antagonized the hyper-activity ensued by the amphetamine.

Overall, the results demonstrate a marked antidopaminergic activity for Compound 3, which may be useful for schizophrenia and related disorders therapy.

Effect of Compound 1 on MK801-induced Hyperactivity in Mice.

As stated above, MK-801 (an NMDA receptor antagonist) is a widely accepted animal model for schizophrenia. The experiment was conducted with Balb/c male mice (Harlan Il), 6 per group. Compound 1 (50 mg/kg) was administered i.p. (1 hr before experimentation), to mice alone or combined with MK-801 (0.15 mg/kg, i.p.) administered 20 minutes prior to placing the mice individually in an open field for 60 minutes. The hyper-active behavior expressed by hyperlocomotion, velocity, strong mobility, number of rearing was evaluated using the Noldus system, each point represents the mean+/−6 determinations.

As FIGS. 8A-E show, at 50 mg/kg Compound 1 induces a clear cut decrease in both basal and MK-801-induced stimulation of horizontal motility as expressed by distance moved, velocity, strong mobility (which is expressed by moving the center of gravidance by more than 30%). Compound 1 also markedly suppressed vertical motility (number of rearings) alone and increased the inhibition of rearings presented by MK-801 as compared to controls. This suggests that Compound 1 has a significant positive modulation effect on the NMDA glutamate receptor.

Figure 9A:
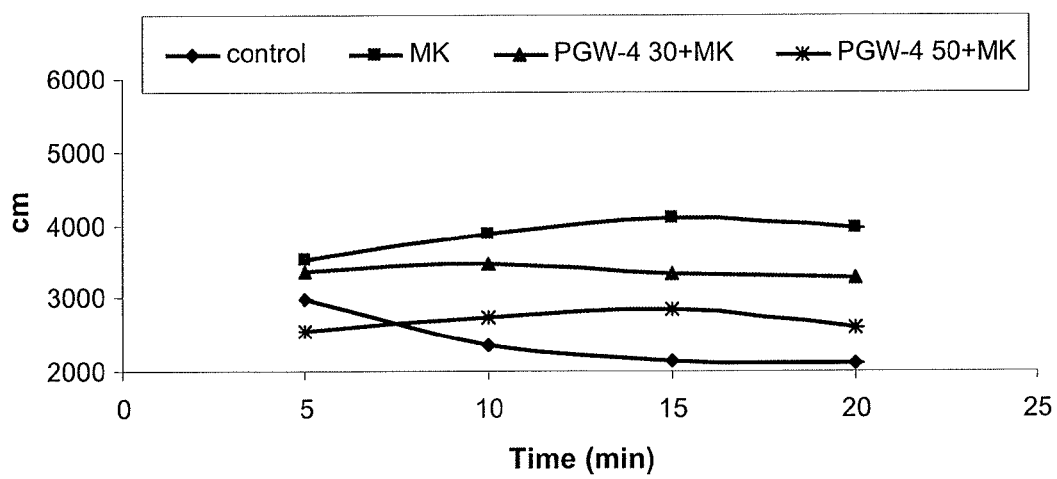
FIGS. 9A-D show the effect of Compound 1 (PGW-4) (administered i.p.) on inhibition of the hyperlocomotion effect of MK-801.
Figure 9B:
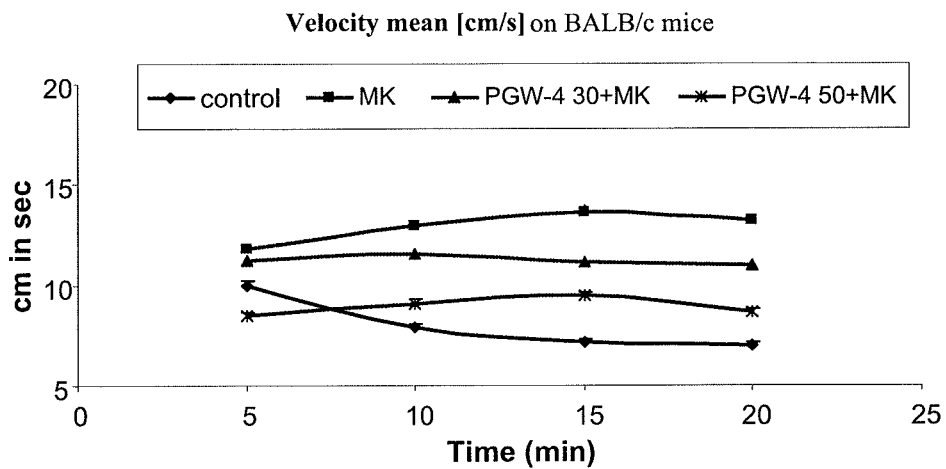
Figure 9C:
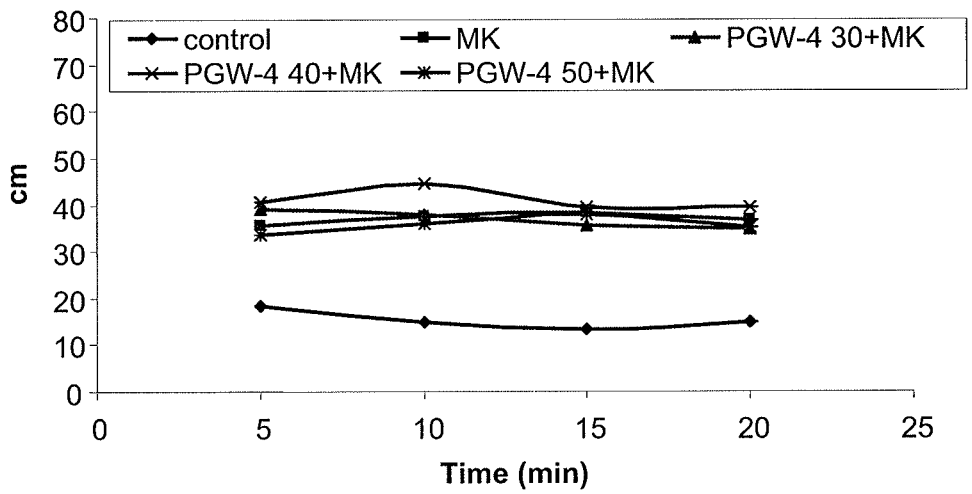
Figure 9D:
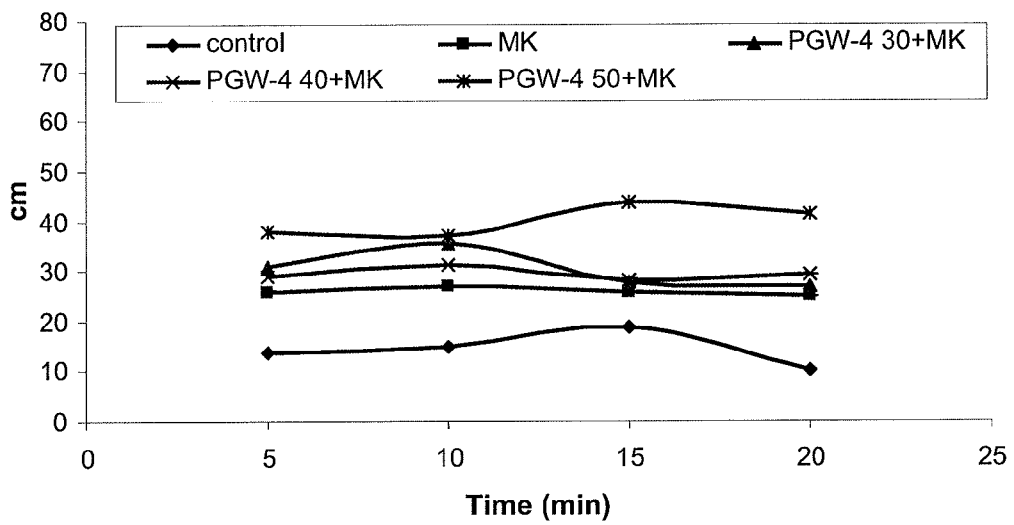

As FIGS. 9A-B show, Compound 1 at 30 and 50 mg/kg, i.p. inhibited in a dose related manner the hyperlocomotion effect of MK-801. FIGS. 10C and D show that Compound 1 at these concentrations did not modify the increased frequency to the center of animals treated with MK-801, and even increased the time spent in the center (zone 3). It can thus be concluded that Compound 1 at high doses antagonizes positive symptoms of MK-801 treated mice, without decreasing the anxiolytic activity of the drug.

Figure 10A:
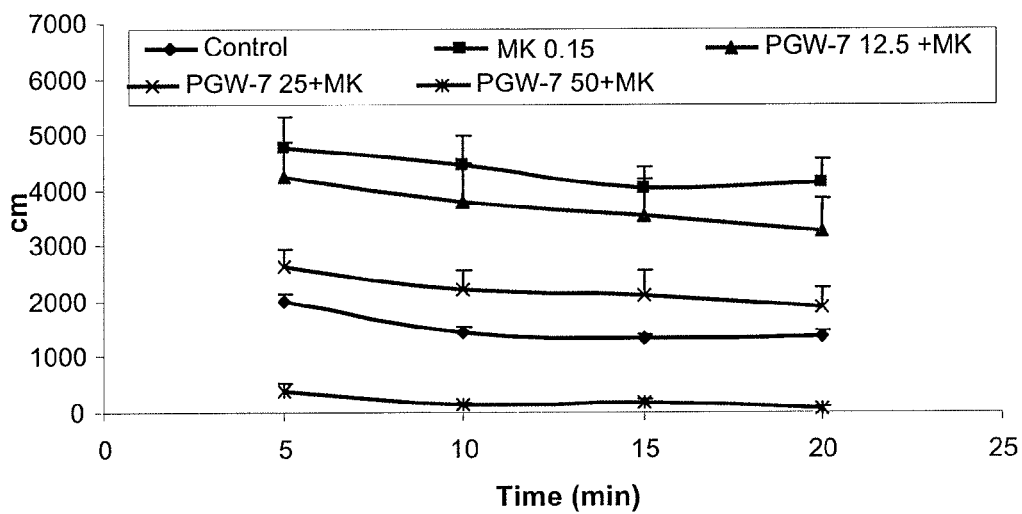
FIGS. 10A-D shows the effect of Compound 3 (PGW-7) (12.5, 25 and 50 mg/kg, i.p.) on hyperactivity-induced by MK-801 (0.15 mg/kg, i.p.).
Figure 10B:
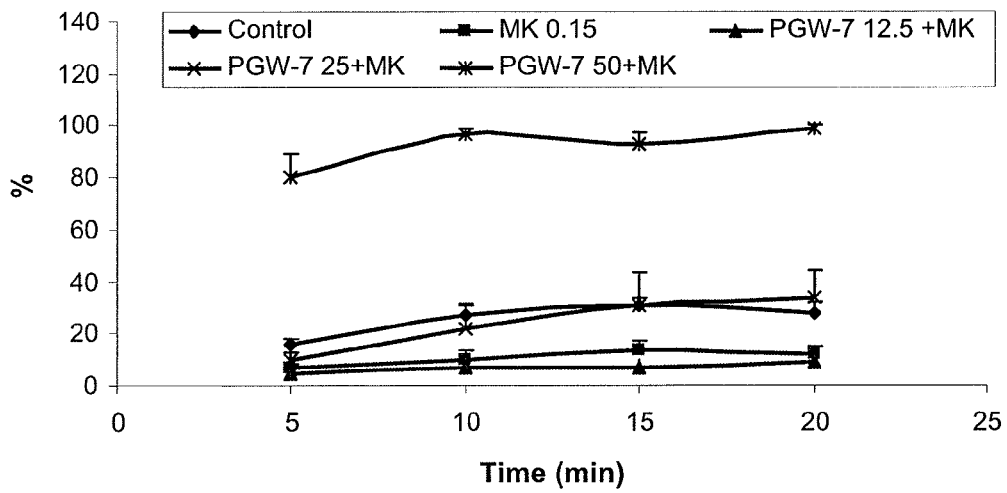
Figure 10C:
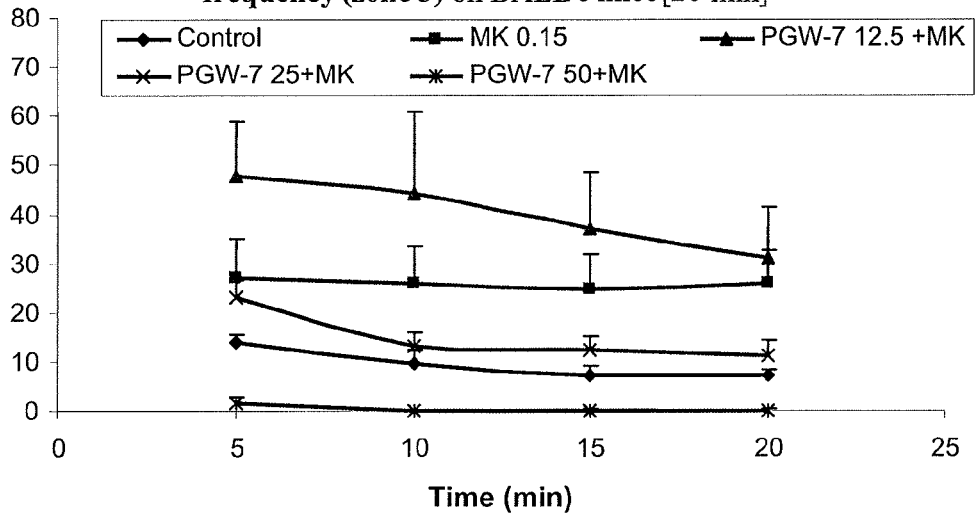
Figure 10D:
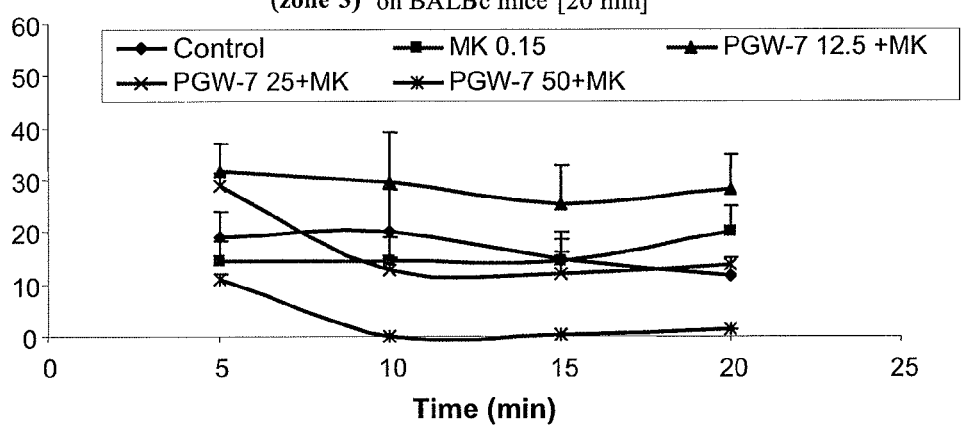

FIGS. 10A-D shows the effect of Compound 3 (12.5, 25 and 50 mg/kg, i.p.) on hyperactivity-induced by MK-801 (0.15 mg/kg, i.p.) in Balb/c mice. The data shows that Compound 3 induced a dose dependent decrease in MK-801-induced hyperactivity, a slight effect was observed with 7.5 mg/kg, normalization of activity was achieved with 25 mg/kg and sedation with 50 mg/kg (FIG. 10A). Immobility was not found with the small and intermediate doses (25 mg/kg) and appeared with the high dose (FIG. 10B). Compound 3 at the low dose tended to increase the frequency to the center of the field (FIG. 10C) and the time spent in the center (FIG. 10D). These results suggest a potential anxiolytic activity for Compound 3.

Effect of Compound 1 at 30-50 Mg/Kg on Catalepsy in Mice

Figure 11:
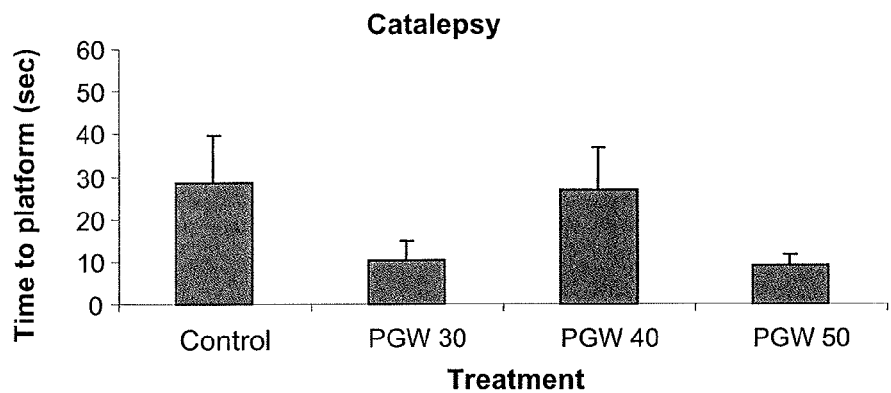
FIG. 11 shows the effect of Compound 1 (PGW) (30, 40 and 50 mg/kg, i.p.) on catalepsy.
Figure 12A:
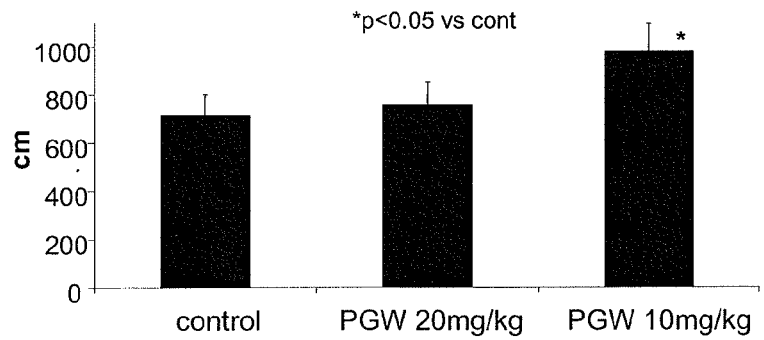
FIGS. 12A-D show the effect of Compound 1 (PGW) (10, 20 mg/kg, oral), in the forced swim test (FST) on distance moved (FIG. 12A); on velocity (FIG. 12B); on strong mobility (FIG. 12C); and on immobility (FIG. 12D).
Figure 12B:
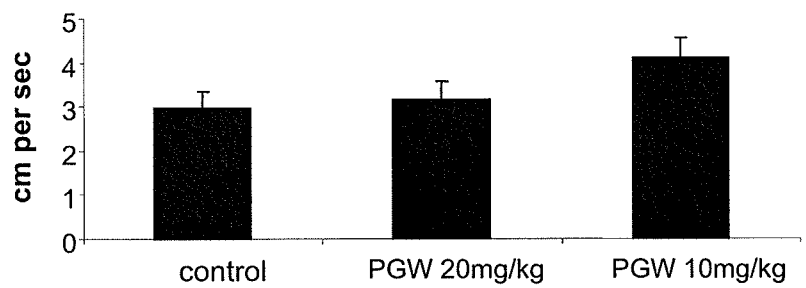
Figure 12C:
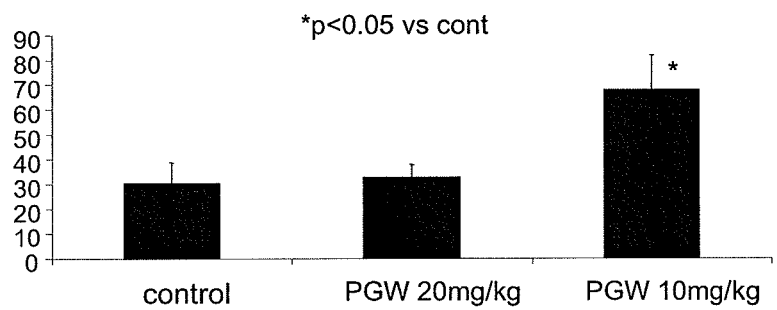
Figure 12D:
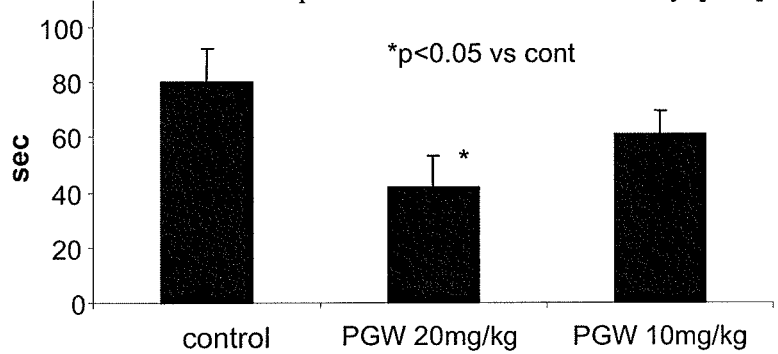
Figure 13A:
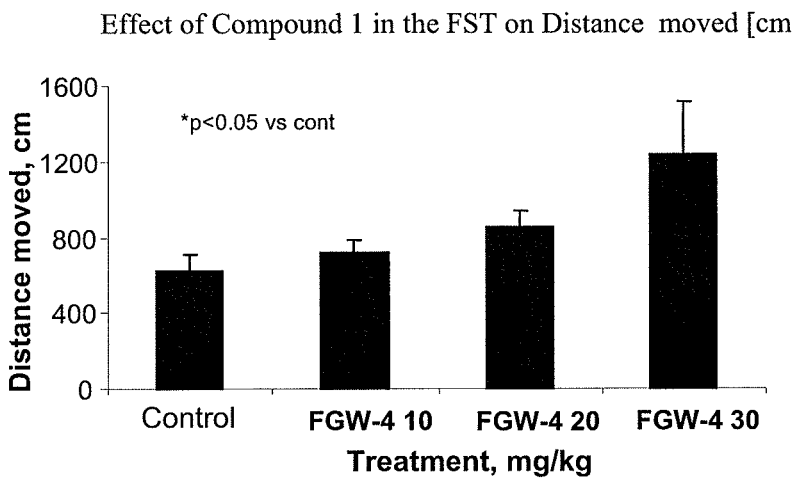
FIGS. 13A-C show the effect of Compound 1 (PGW-4) (10, 20, 30 mg/kg, oral) in the FST on immobility (FIG. 13A); on distance moved (FIG. 13B); and on strong mobility (FIG. 13C).
Figure 13B:
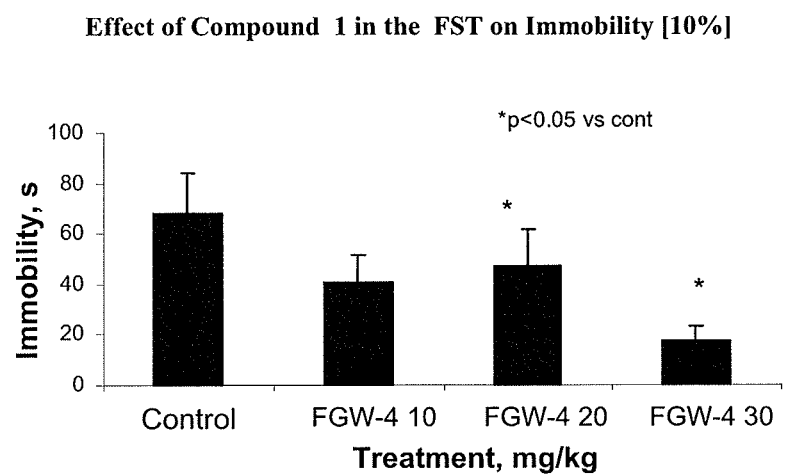
Figure 13C:
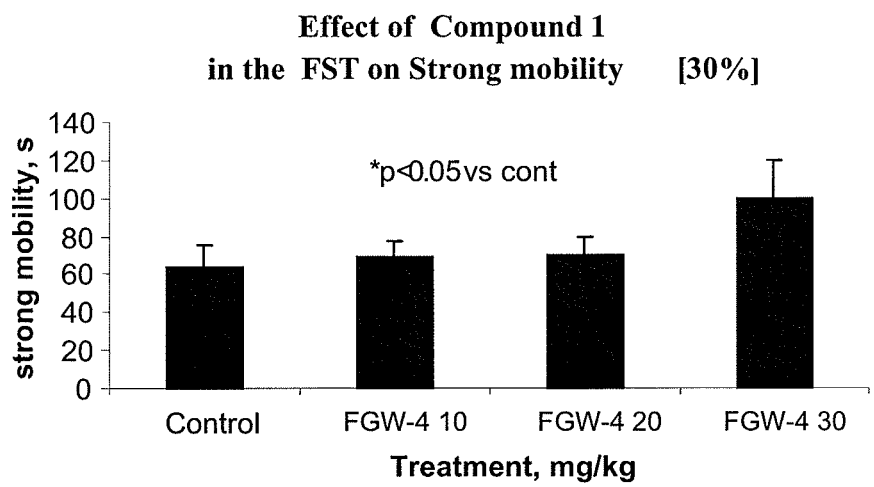

As FIG. 11 shows, Compound 1 at doses of up to 50 mg/kg did not induce catalepsy in mice. This suggests that at doses which are efficacious against positive symptoms of schizophrenia there is no catalepsy or extrapyramidal symptoms induced by Compound 1.

Effect of Compound 1 on the Forced Swim Test (FST)

Males Balb/c mice (Harlan Israel) were used. Animals were administered orally with Compound 1 (10 or 20 mg/kg) or with a vehicle. The results shown in FIGS. 12A-D and FIGS. 13A-C demonstrate that orally administered Compound 1 at 10 mg/kg significantly increased the distance moved (swimming behavior) and strong mobility (climbing behavior) and at 20 mg/kg decreased immobility as compared to vehicle treated animals. The results suggest a significant antidepressant activity for Compound 1 as appears in the forced swim test.

Comparison Between the Activity of Compound 1 and Olanzapine

Figure 14A:
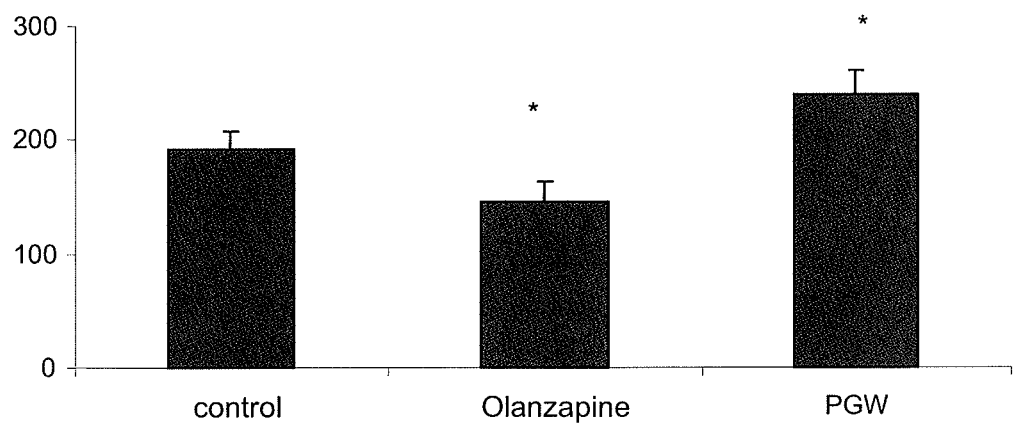
FIGS. 14A-B show the effect of olanzapine in comparison to Compound 1 (PGW) in the FST on distance moved (FIG. 14A) and immobility (FIG. 14B).
Figure 14B:
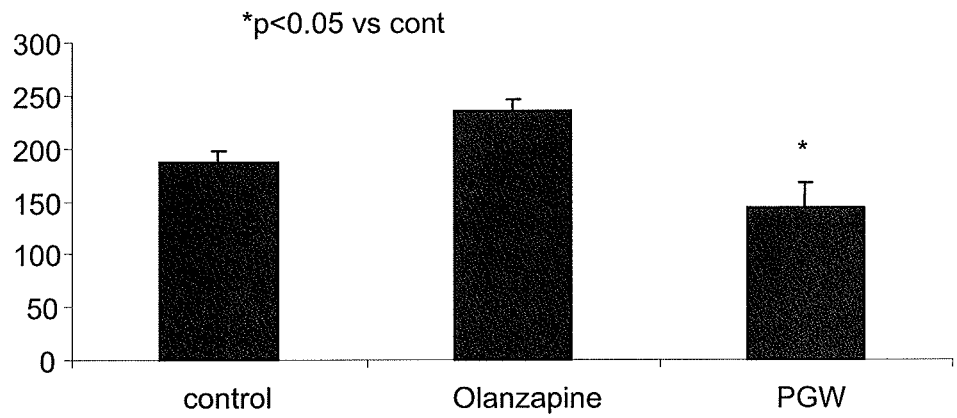

Males ICR mice were used. Animals were administered orally with olanzapine or Compound 1 (20 mg/kg) or with a vehicle. The results shown in FIGS. 14A-B indicate that orally administered olanzapine at 20 mg/kg significantly decreased distance moved, velocity and strong mobility (climbing) and increased immobility. Compound 1 at the same dose did not modify velocity and distance moved, and significantly decreased strong mobility (climbing) and immobility compared to vehicle and to olanzapine in treated animals. These data suggest that Compound 1 is different from olanzapine, and at 20 mg/kg it causes decrease in immobility, suggesting a potential antidepressant activity.

Effect of Compound 1 on Anxiety in the Elevated Plus Maze

Figure 15A:
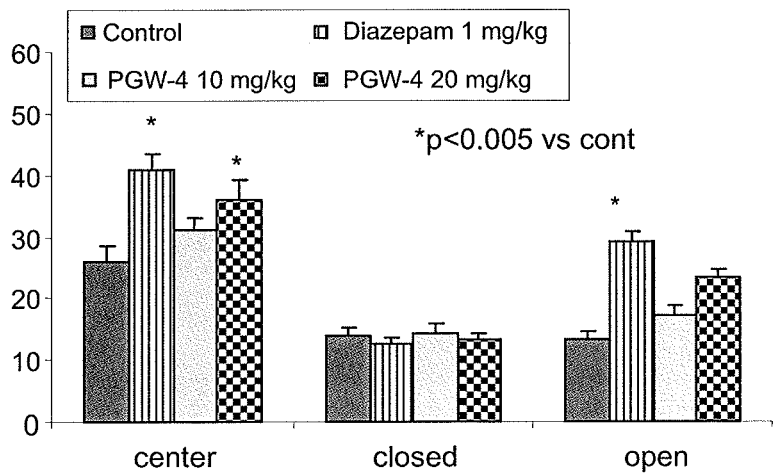
FIGS. 15A-E show the effect of Compound 1 (PGW-4) and diazepam in the elevated plus maze test on mice frequency in-zone (FIG. 15A); on total duration in zone (FIG. 15B); on velocity (FIG. 15C); and rearing frequency (FIG. 15D).
Figure 15B:
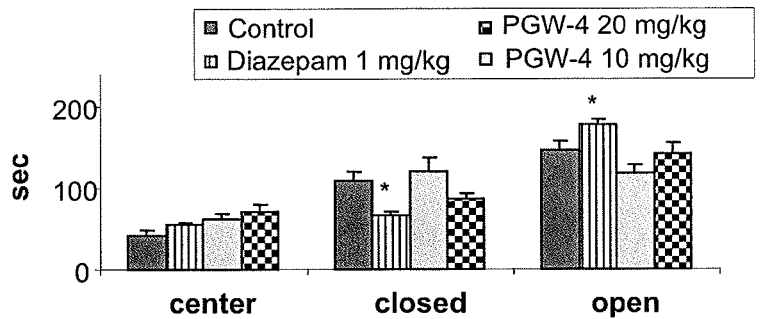
Figure 15C:
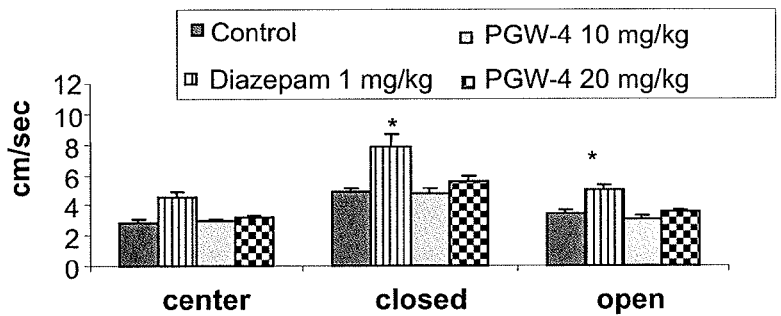

Male Balb/c mice were used. Animals were transferred to the behavior room 24 hr before the experiment. Compound 1 or diazepam were administered orally 90 minutes before testing. Each treatment group included 5 animals. FIG. 15A shows the effect of Compound 1 on frequency of the mice to the different arms. The results show that mice treated with Compound 1 (20 mg/kg) frequented significantly more the open arm and the center resembling the mice treated with diazepam at 1 mg/kg. FIG. 15B shows the effect of Compound 1 on duration of time spent in the different zones of the elevated plus maze. At 20 mg/kg Compound 1 increased the time spent in the center, but did not significantly affect the time spent in the closed and the open arm at variance from diazepam. FIG. 15C shows the velocity of the mice which was higher in the mice treated with diazepam but not in the mice treated with Compound 1.

Figure 15D:
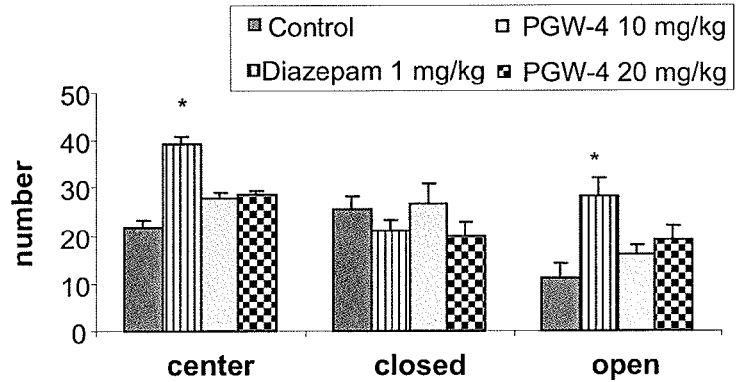

FIG. 15D shows the frequency of rearings of mice treated with Compound 1, diazepam or controls. The results show increased number of rearings in the open aim in the diazepam and the Compound 1 treated groups. As may be noted, diazepam significantly increased the number of rearings also in the center.

From the above it may be concluded that at 20 mg/kg Compound 1 showed anxiolytic activity which resembles diazepam, but differs from it in its intensity and in the effects on velocity.

Figure 15E:
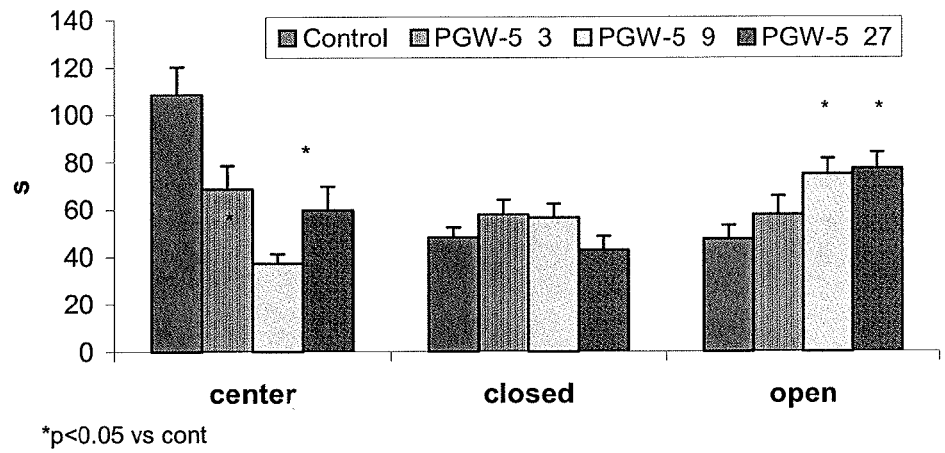

FIG. 15E shows the total time spent by the mice administered with Compound 6 (3, 9 and 27 mg/kg, orally) on the different arms of the maze. The results demonstrate that mice treated with Compound 6 spent more time on the open arms and less on the center, suggesting a potential anxiolytic activity for the Compound.

Effect of Compound 1 on Spatial Cognition in the Morris Water Maze

The Morris Water Maze is a well known test aimed to assess spatial cognitive tasks. The maze consists of a circular pool measuring 1.80 m in diameter 60 cm in height. The pool was filled with water (21±1° C.) to a depth of 30 cm. A circular hidden escape platform (10 cm in diameter) was placed just below the water surface. The test room contained several permanent extra maze cues such as the rat housing rack, laboratory table, posters on the walls, etc.

In the experiment rats were given Compound 1 orally on day 1 and the first test begun 90 minute later, six trials per day, for 3 consecutive days, to find the hidden platform (acquisition phase). The escape latency, i.e., the time required by the rat to find and climb onto the platform, was recorded for up to 120 sec. Each rat was allowed to remain on the platform for 30 sec, after which it was removed to its home cage. If the rat did not find the platform within 120 sec, it was manually placed on it and returned to its home cage after 30 sec.

A video camera was placed above the center of the pool for tracking the rat, and a video tracking system (Noldus) with online digital output directly fed data into a computer. Data were analyzed using EthoVision automated tracking system software (Noldus).

Figure 16:
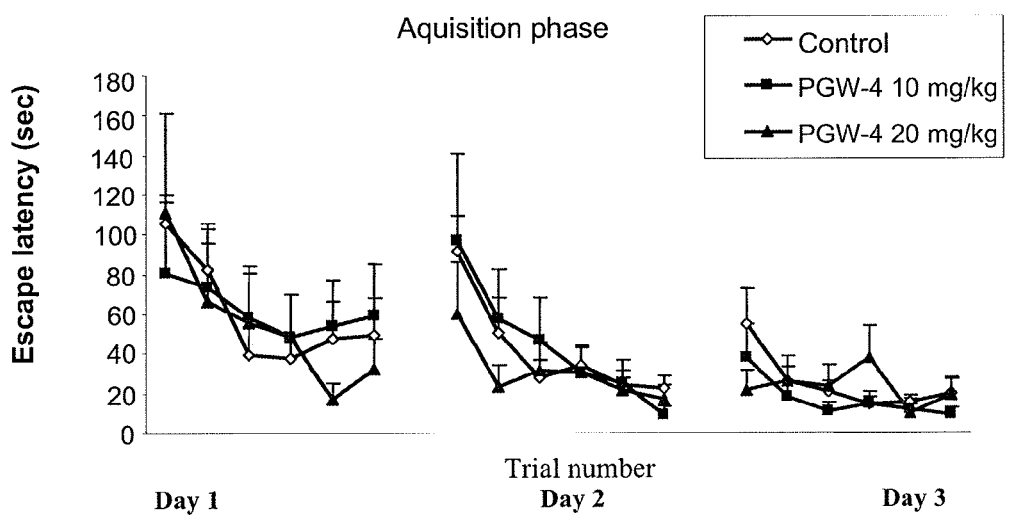
FIG. 16 shows the effect of 10 and 20 mg/kg of Compound 1 (PGW-4), administered p.o. on latency to platform.

FIG. 16 shows the effect of 10 and 20 mg/kg of Compound 1, administered po, on latency to platform. Compound 1 at 20 mg/kg showed a faster learning on the first day of the spatial task and reached the platform earlier. Also on the second day, an improvement was noticed of task execution by mice treated with Compound 1 (20 mg/kg). On the third day, no difference was found between all groups, and all rats reached rapidly the platform. These results clearly suggest that Compound 1 can enhance cognitive tasks in the rats.

Figure 17:
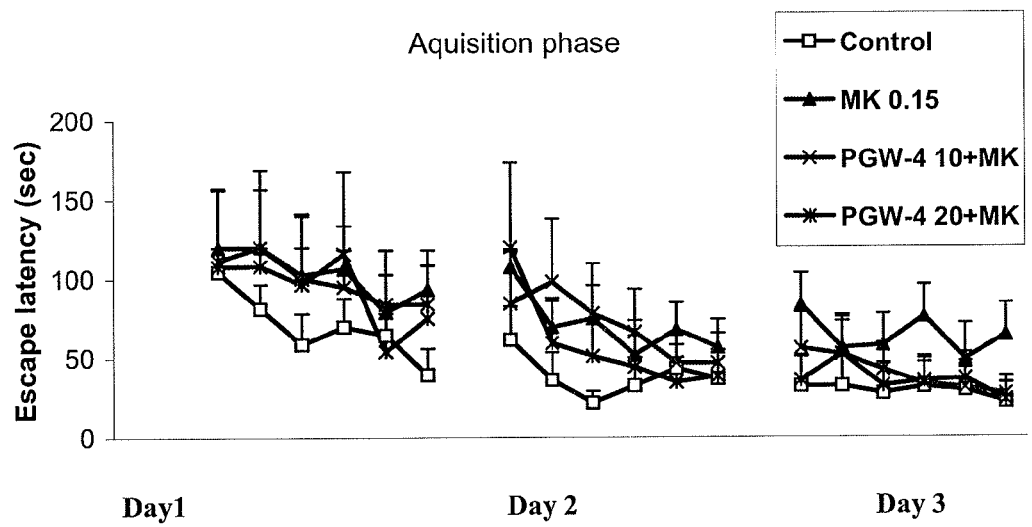
FIG. 17 shows the effect of acute treatment of Compound 1 at 10 and 20 mg/kg given p.o. on the spatial cognitive tasks in the Morris Water Maze in rats pretreated with MK-801.

FIG. 17 shows the effect of acute use of Compound 1 at 10 and 20 mg/kg given p.o. on day 1 on the spatial cognitive tasks in the Morris Water Maze in rats pretreated (−30 minutes) with MK-801 (on day 1) at 0.15 mg/kg, i.p. MK-801 alone induced a significant impairment in the memory tasks of the rats as expressed by increased latency to the platform as compared to the normal controls. Compound 1 at both doses decreased the latency to the platform on day 3 of the experiment but not on days 1 and 2. These results may thus provide an indication as to the ability of Compound 1 to relief some of the cognitive impairments observed in states of schizophrenia due to decreased NMDA activity.

Figure 18:
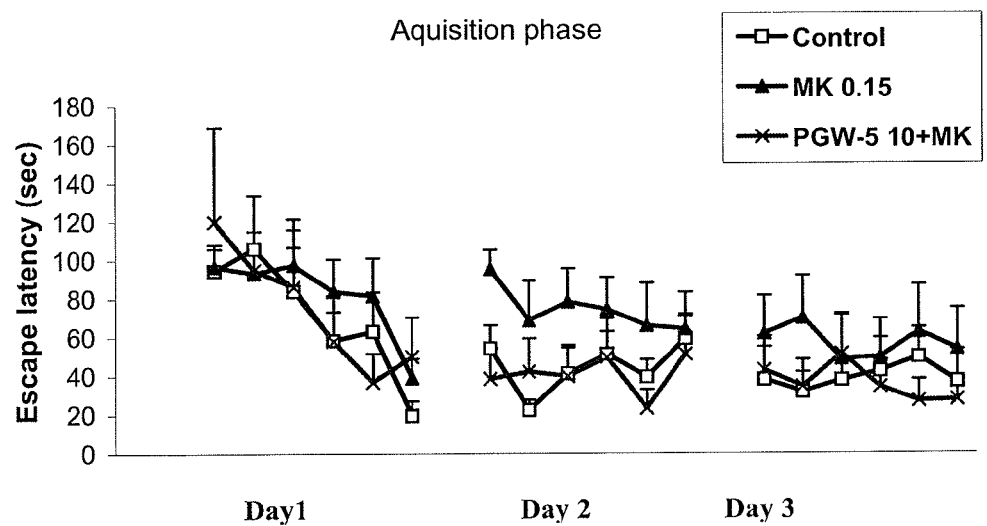
FIG. 18 shows the effect of acute use of Compound 6 at 10 mg/kg given p.o. on the spatial cognitive tasks in the Morris Water Maze in rats pretreated with MK-801.

The relief of cognitive impairments was also shown in the use of Compound 6. FIG. 18 shows the effect of acute use of Compound 6 at 10 mg/kg given p.o. once on day 1 on the spatial cognitive tasks in the Morris Water Maze in rats pretreated (−30 minutes) with MK-801 (0.15 mg/kg, i.p.). MK-801 alone induced a significant impairment in the memory tasks of the rats as expressed by increased latency to the platform as compared to the normal controls. Compound 6 at 10 mg/kg decreased the latency to the platform on days 2 and 3 of the experimentation. In similarity with Compound 1, the described use of Compound 6 suggests use in relieving some of the cognitive impairments seen in states of schizophrenia due to decreased NMDA activity.

Overall and without wishing to be bound by theory, the effects of Compound 1 and 6 on spatial memory suggest a common mechanism for both effective activity on NMDA blockage and dopamine overshooting, and parallel stimulation of negative symptoms associated with cognitive impairment.

Effect of Compound 6 on Anxiety in the EPM Apparatus

Male Balb/c mice were used. Animals were transferred to the behavior room 24 hr before the experiment. Compound 6 (3, 9, or 27 mg/kg) or vehicle were administered orally 90 minutes before testing. Each treatment group included 5 animals. The effect of Compound 6 on duration of time spent in the different zones of the elevated plus maze is evident from the dose-dependently increase in the time spent in the open arms and decrease in the time spent in the center. The drug did not significantly affect the time spent in the closed arm. This suggests that Compound 6 has an anxiolytic activity.

Subchronic Toxicity

Figure 19:
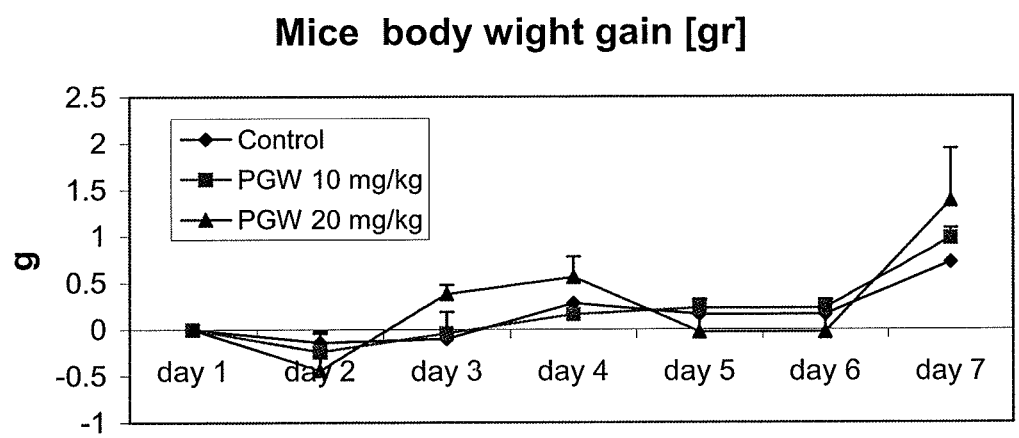
FIG. 19 shows the effect of Compound 1 on the mice body weight.

Subchronic toxicity was tested in ICR male mice. Animals (5 per group) received Compound 1 daily (10 and 20 mg/kg p.o). Animals were followed up for 7 days; weight, food intake and water intake were registered. As shown in FIG. 19, no difference compared to control animals in body weight, food intake and water intake was found.

The drug was well tolerated, and no apparent difference was found also in animal general behavior. Further results showed that Compound 1 did not cause toxic effect up to 20 mg/kg given for 7 days.

In-Vitro Toxicity

Since glutamate is known to possess a neurotoxic effect, the in-vitro effect of Compound 1 was evaluated as compared to olanzapine, paroxetine and sertraline on human glioma U83 cell viability. Cells were treated with Compound 1, olanzapine, paroxetine, or sertraline as compared to controls (saline treated cells), 24 hr after exposure to the drug. Determination of cell viability was performed in cells (10,000/well) using neutral red method. Absorption of neutral red by lysosomes caused coloring of living cells. Quantitative analysis was performed by colorimetric assay (ELISA reader at 550 nm).

Figure 20:
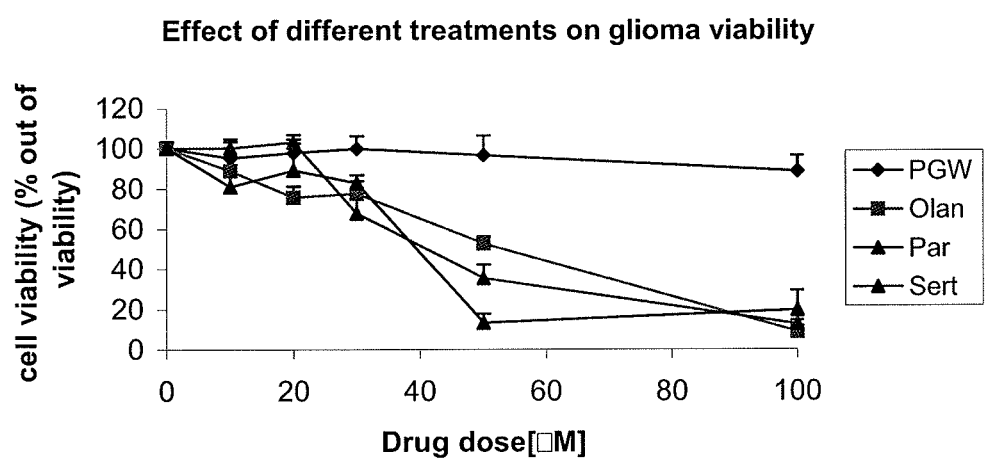
FIG. 20 shows the effect of treatments with different drugs on glioma viability.

The results shown in FIG. 20 demonstrate that Compound 1 is not toxic up to 100 µM to human glioma cells. Olanzapine, sertraline and paroxetine at concentrations higher than 30 µM induced a dose dependent decrease in cell viability. Overall, the results suggest that Compound 1 as the other compounds of the invention are well tolerated and possess low toxicity as presented by the in vivo and the in vitro assays detailed herein.

The invention claimed is:

1. A compound, or a salt or stereoisomer thereof, of the general formula L-M-V, wherein L is clozapine;

M is optionally present and is a linker selected from the group consisting of —NH—, —O—, —S—, $C_1$-$C_8$-alkylene, $C_3$-$C_8$-cycloalkylene, —$CH_2$—O—$CH_2$, —(CH$_2$)$_n$—O—(CH$_2$)$_n$—, —(CH$_2$—O)$_n$—, and —(CH$_2$CH$_2$—O)$_n$—, said alkylene and cycloalkylene being optionally substituted by one or more groups selected from the group consisting of C$_1$-C$_4$ alkyl, C$_2$-C$_4$ alkenyl, and C$_2$-C$_4$ alkynyl;

V is a modulator of a glutamate N-methyl-D-aspartate (NMDA) receptor selected from the group consisting of an amino acid, an ester of the amino acid, an amide of the amino acid, and an alkylated amine of the amino acid; wherein said amino acid is selected from the group consisting of glycinyl, sarcosinyl, serinyl, and cysteinyl;

n, independently of each other, is an integer from 0 to 3; and

L is conjugated to M-V through an N—CH$_2$ group present at the piperazine end of clozapine.

2. The compound, or a salt or stereoisomer thereof, according to claim 1, wherein said linker is selected from the group consisting of —NH—, —O—, —S—, —(CH$_2$)$_m$— wherein m is an integer between 1 and 8, —(CH$_2$—CH=CH—CH$_2$)—, —(CH=CH$_2$—CH$_2$—CH$_2$)—, —(CH$_2$—CH=CH—CH$_2$—CH$_2$—CH$_2$)—, —(CH$_2$—C≡C—CH$_2$)—, —(C≡C—CH$_2$—CH$_2$)—, —(CH$_2$—NH—CH=CH—CH$_2$)—, —(CH$_2$—NH—CH$_2$—CH$_2$—CH$_2$)—, —(CH$_2$—O—CH$_2$—CH$_2$)—, —(CH$_2$)$_n$—O—(CH$_2$)$_n$—, —CH$_2$—O—CH$_2$—, —(CH$_2$—O)$_n$—, and —(CH$_2$CH$_2$—O)$_n$— wherein n is an integer from 0 to 3, and substituted derivatives thereof.

3. The compound, or a salt or stereoisomer thereof, according to claim 1, wherein the bonds between M and L and between M and V are non-hydrolizable.

4. The compound, or a salt or stereoisomer thereof, according to claim 1, wherein the compound is selected from the group consisting of:

| Compound No. | L | M | N |
|---|---|---|---|
| 18 | Clo | absent | —CH(NH$_2$)(COOCH$_3$) |
| 19 | Clo | absent | —CH(NH$_2$)(COOCH$_2$CH$_3$) |
| 20 | Clo | —OCH$_2$— | —CH(NH$_2$)(COOCH$_3$) |
| 21 | Clo | —OCH$_2$— | —CH(NH$_2$)(COOCH$_2$CH$_3$) |
| 22 | Clo | absent | —CH(NHCH$_3$)(COOH) |
| 23 | Clo | absent | —CH(NHCH$_3$)(COOCH$_3$) |
| 24 | Clo | absent | —CH(NHCH$_3$)(COOCH$_2$CH$_3$) |
| 25 | Clo | absent | —C(NH$_2$)(CH$_2$OH)(COOH) |
| 26 | Clo | absent | —C(NH$_2$)(CH$_2$OH)(COOCH$_3$) |
| 27 | Clo | absent | —C(NH$_2$)(CH$_2$OH)(COOCH$_2$CH$_3$) |
| 28 | Clo | —OCH$_2$— | —CH(NHCH$_3$)(COOH) |
| 29 | Clo | —OCH$_2$— | —CH(NHCH$_3$)(COOCH$_3$) |
| 30 | Clo | —OCH$_2$— | —CH(NHCH$_3$)(COOCH$_2$CH$_3$) |
| 31 | Clo | —CH$_2$CH$_2$OCH$_2$— | —CH(NH$_2$)(COOCH$_3$) |
| 32 | Clo | —CH$_2$CH$_2$OCH$_2$— | —CH(NH$_2$)(COOCH$_2$CH$_3$) |
| 33 | Clo | —CH$_2$CH$_2$OCH$_2$— | —CH(NHCH$_3$)(COOCH$_3$) |
| 34 | Clo | —CH$_2$CH$_2$OCH$_2$— | —CH(NHCH$_3$)(COOCH$_2$CH$_3$). |

5. A composition comprising at least one compound, or a salt or stereoisomer thereof, according to claim 1 and a carrier.

6. The composition according to claim 5, being a pharmaceutical composition.

7. The composition according to claim 6, being suitable for oral, aerosol, parenteral, subcutaneous, intravenous, intramuscular, interperitoneal, rectal, or vaginal administration.

8. A method for treating disease or disorder, the method comprising administering to a subject in need thereof the pharmaceutical composition according to claim 6, wherein said disease or disorder is selected from the group consisting of schizophrenia, anxiety, and depression.

9. A method for treating a disease or disorder, the method comprising administering to a subject in need thereof the compound, or a salt or stereoisomer thereof, according to claim 1, wherein said disease or disorder is selected from the group consisting of anxiety and depression.

10. A method for treating schizophrenia, said method comprising administering to a person suffering from schizophrenia or symptoms associated therewith an effective amount of the compound, or a salt or stereoisomer thereof, according to claim 1.

11. The compound, or a salt or stereoisomer thereof, according to claim 4, wherein the compound is Compound No. 18.

* * * * *

UNITED STATES PATENT AND TRADEMARK OFFICE
CERTIFICATE OF CORRECTION

| | | |
|---|---|---|
| PATENT NO. | : 8,828,993 B2 | Page 1 of 1 |
| APPLICATION NO. | : 13/748861 | |
| DATED | : September 9, 2014 | |
| INVENTOR(S) | : Moshe Portnoy et al. | |

It is certified that error appears in the above-identified patent and that said Letters Patent is hereby corrected as shown below:

In the Claims:

In Column 40, line 67, change "-$CH_2$-O-$CH_2$," to -- -$CH_2$-O-$CH_2$-,--.

In Column 41, line 37, change "N" to --V--.

In Column 42, line 5, change "N" to --V--.

Signed and Sealed this
Seventh Day of April, 2015

Michelle K. Lee
*Director of the United States Patent and Trademark Office*